US011389421B2

(12) United States Patent
Emgenbroich et al.

(10) Patent No.: US 11,389,421 B2
(45) Date of Patent: Jul. 19, 2022

(54) TRANSDERMAL THERAPEUTIC SYSTEM FOR THE TRANSDERMAL ADMINISTRATION OF RIVASTIGMINE

(71) Applicant: LTS LOHMANN THERAPIE-SYSTEME AG, Andernach (DE)

(72) Inventors: Marco Emgenbroich, Rheinbach (DE); Nico Reum, Mendig (DE); Jessica Verstraelen, Wolfsburg (DE); Regine Kaufmann, Neuwied (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 16/641,747

(22) PCT Filed: Sep. 4, 2018

(86) PCT No.: PCT/EP2018/073736
§ 371 (c)(1),
(2) Date: Feb. 25, 2020

(87) PCT Pub. No.: WO2019/048425
PCT Pub. Date: Mar. 14, 2019

(65) Prior Publication Data
US 2020/0261394 A1  Aug. 20, 2020

(30) Foreign Application Priority Data
Sep. 5, 2017  (EP) .................... 17189352

(51) Int. Cl.
A61K 31/27  (2006.01)
A61K 9/70  (2006.01)
(52) U.S. Cl.
CPC ............ A61K 31/27 (2013.01); A61K 9/7069 (2013.01)
(58) Field of Classification Search
CPC .......... A61P 25/28; A61P 25/16; A61P 25/00; A61P 25/08; A61P 25/14; A61P 25/22; A61P 25/24; A61P 25/30; A61P 25/36; A61P 43/00; A61P 9/10; A61P 25/04; A61P 25/26; A61P 25/18; A61P 9/12; A61P 11/00; A61P 17/00; A61P 1/04; A61P 1/08; A61P 25/06; A61P 29/00; A61P 31/00; A61P 33/06; A61P 37/08; A61P 3/10; A61P 5/00; A61P 9/00; A61P 11/02; A61P 1/06; A61P 21/00; A61P 25/02; A61P 27/02; A61P 31/10; A61P 3/00; A61P 3/02; A61P 3/04; A61P 5/26; A61P 5/30; A61P 13/10; A61P 17/02; A61P 25/20; A61P 15/18; A61P 31/18; A61K 9/7061; A61K 31/27; A61K 9/7069; A61K 31/13; A61K 9/7084; A61K 45/06; A61K 9/0097; A61K 9/703; A61K 9/7053; A61K 31/485; A61K 47/02; A61K 31/165; A61K 31/465; A61K 47/32; A61K 2300/00; A61K 31/407; A61K 9/7023; A61K 31/167; A61K 31/192; A61K 31/4725; A61K 31/565; A61K 31/155; A61K 31/46; A61K 47/12; A61K 47/6957; A61K 31/4748; A61K 47/08; A61K 47/10; A61K 47/14; A61K 9/70; A61K 31/137; A61K 31/12; A61K 31/122; A61K 31/203; A61K 31/343; A61K 31/4166; A61K 31/4412; A61K 31/555; A61K 31/573; A61K 31/616; A61K 47/34; A61K 9/0024; A61K 9/0092; A61K 31/131; A61K 31/4168; A61K 31/4458; A61K 31/4525; A61K 31/428; A61K 31/445; A61K 9/0014; A61K 9/0036; A61K 9/127; A61K 9/4866; A61K 9/5026; A61M 2205/3592; A61M 2207/00; A61M 37/00; A61M 2025/1004; A61M 2025/105; A61M 2205/0216; A61M 25/0017; A61M 25/1002; A61M 31/002; C08F 220/1808; C08F 218/08; C08F 220/56; C08F 220/26; C08F 220/281; C08F 220/282; C08F 220/285; C08F 230/08; C08L 33/10; C08L 75/04; C08L 33/00; C08L 33/06; C08L 83/04; C08J 133/08; C08J 133/10; C08J 4/06; C08J 133/06; C08J 133/14; C08J 133/24
See application file for complete search history.

(56) References Cited

U.S. PATENT DOCUMENTS

2012/0114737 A1* 5/2012 Loubert .................. A61P 25/06
                                                    424/445
2014/0271866 A1  9/2014 Ryoo
2016/0030362 A1* 2/2016 Liao .................... A61K 31/4168
                                                    424/448

FOREIGN PATENT DOCUMENTS

EP  2292219 B1  6/2013
EP  2599847 A1  6/2013
(Continued)

OTHER PUBLICATIONS

International Search Report for International Application No. PCT/EP2018/073736, European Patent Office, Netherlands, dated Oct. 18, 2018, 2 pages.

Primary Examiner — Audrea B Coniglio
(74) Attorney, Agent, or Firm — Sterne, Kessler, Goldstein & Fox P.L.L.C.

(57) ABSTRACT

The present invention relates to a transdermal therapeutic system (TTS) for the transdermal administration of rivastigmine comprising a rivastigmine-containing layer structure, said rivastigmine-containing layer structure comprising: A) a backing layer; and B) a rivastigmine-containing layer.

15 Claims, 4 Drawing Sheets

(56) References Cited

FOREIGN PATENT DOCUMENTS

| | | |
|---|---|---|
| WO | WO 2007145996 A2 | 12/2007 |
| WO | WO 2010124187 A2 | 10/2010 |
| WO | WO 2016130408 A1 | 8/2016 |

* cited by examiner

TRANSDERMAL THERAPEUTIC SYSTEM FOR THE TRANSDERMAL ADMINISTRATION OF RIVASTIGMINE

TECHNICAL FIELD OF THE INVENTION

The present invention relates to a transdermal therapeutic system (TTS) for the transdermal administration of rivastigmine to the systemic circulation, and processes of manufacture, method of treatments and uses thereof.

BACKGROUND OF THE INVENTION

The active agent rivastigmine (also known as e.g. (S)-3-[1-(dimethylamino)ethyl]phenyl ethylmethylcarbamate or CAS No. 123441-03-2) is a parasympathomimetic or cholinergic agent belonging to the family of phenyl carbamate. It has the following chemical formula.

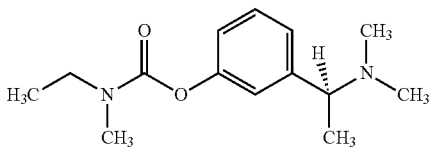 [SMILES: CCN(C)C(=O)Oc1cccc([C@H](C)N(C)C)c1]

Rivastigmine inhibits both butyrylcholinesterase and acetylcholinesterase. In general, rivastigmine is used for the treatment of mild to moderate dementia of the Alzheimer's type and dementia due to Parkinson's disease.

Currently, rivastigmine is commercially available, e.g., in the form of capsules and in the form of transdermal therapeutic systems.

A transdermal therapeutic system, which is commercially available under the name Exelon® has an area of release of 2.5, 5, 7.5, 10, 15, or 20 $cm^2$. According to EP 2292219 B2, the TTS comprises three layers in the following order: (1) a backing layer, (2) a rivastigmine-containing layer comprising acrylate polymers, and (3) an adhesive layer free of rivastigmine comprising a silicone adhesive.

Exelon® comprises, depending on the patch size, 4.5, 9, 13.5, 18, 27, or 36 mg of rivastigmine. The TTS is designed to deliver approximately 2.3, 4.6, 6.7, 9.5, 13.3, or 17.4 mg of rivastigmine over a 24-hour period.

One problem in connection with Exelon® is that the currently available patches tend to cause skin irritation. Furthermore, an economic disadvantage of the Exelon® patch is the process of manufacturing, as the patch comprises two different adhesive layers on the backing layer, which makes the process of manufacturing more complex.

It is therefore desirable to provide a TTS, which has a less complex structure in comparison to Exelon®, and is therefore less costly in terms of the manufacture.

OBJECTS AND SUMMARY OF THE INVENTION

It is an object of the present invention to provide a TTS for the transdermal administration of rivastigmine, which is improved in comparison to the current commercially available rivastigmine TTS Exelon®.

It is a further object of the present invention to provide a TTS for the transdermal administration of rivastigmine with a less complex structure than the current commercially available rivastigmine TTS, e.g., a TTS comprising only a backing layer and a rivastigmine-containing layer, so that the costs and the complexity of the manufacture of the TTS can be reduced in comparison to the prior art. At the same time, it is an object that the TTS with the less complex structure provides suitable drug delivery properties and plasma concentrations, during an administration period to the skin of the patient for at least 12 hours, preferably about 24 hours (1 day).

It is a further object of the present invention to provide a TTS for the transdermal administration of rivastigmine with a more constant and continuous rivastigmine delivery.

It is an object of the present invention to provide a TTS for the transdermal administration of rivastigmine, which delivers approximately 150 to 3500 $\mu g/cm^2$ of rivastigmine at an approximately constant rate during an administration period of the TTS to the skin of the patient for at least 12 hours, preferably about 24 hours (1 day).

It is another object of the present invention to provide a TTS for the transdermal administration of rivastigmine, which provides comparable delivery properties, such as therapeutically effective plasma concentration, of rivastigmine compared to the current commercially available rivastigmine TTS Exelon®.

It is a further object of certain embodiments of the present invention to provide a TTS, for the transdermal administration of rivastigmine, wherein therapeutically effective plasma concentrations of rivastigmine are provided by said transdermal therapeutic system during an administration period to the skin of the patient for 24 hours, allowing an exchange of the TTS every day.

It is a further object of the present invention to provide a TTS for the transdermal administration of rivastigmine, which is suitable for use in a method of preventing, treating, or delaying of progression of Alzheimer's disease, dementia associated with Parkinson's disease, and/or symptoms of traumatic brain injury, or for use in a method of treating mild to moderate dementia caused by Alzheimer's or Parkinson's disease.

It is another object of the present invention to provide a TTS for the transdermal administration of rivastigmine without causing significant skin irritation problems.

It has now surprisingly been found that at least one of these objects and others are accomplished by the present invention, which according to one aspect relates to a transdermal therapeutic system for the transdermal administration of rivastigmine, comprising a rivastigmine-containing layer structure, said rivastigmine-containing layer structure comprising:

A) a backing layer; and
B) a rivastigmine-containing layer;

wherein the transdermal therapeutic system comprises a silicone acrylic hybrid polymer.

It has been found that the TTS according to the present invention, which comprises a silicone acrylic hybrid polymer, provides advantageous properties in terms of the constant and continuous rivastigmine delivery. Moreover, the TTS requires a less complex structure than Exelon®, which comprises two layers on the backing layer as explained above. Instead, the TTS according to the present invention provides suitable permeation rates and suitable permeated amounts of rivastigmine over a 24-hour period, even if the TTS comprises only a backing layer and a rivastigmine-containing layer, preferably a rivastigmine-containing matrix layer. In particular, it is not required to use a rate-controlling membrane. Accordingly, the TTS according to the present invention has a structure of low complexity and is less costly in terms of the manufacture than Exelon®.

According to certain embodiments, the invention also relates to a transdermal therapeutic system for the transdermal administration of rivastigmine as described above, wherein the rivastigmine-containing layer is a rivastigmine-containing matrix layer comprising:
1. rivastigmine, and
2. the silicone acrylic hybrid polymer.

According to one specific aspect, the present invention relates to a transdermal therapeutic system for the transdermal administration of rivastigmine, comprising a rivastigmine-containing layer structure, said rivastigmine-containing layer structure comprising:
A) a backing layer; and
B) a rivastigmine-containing layer comprising:
1. rivastigmine in an amount of from 10 to 25% by weight based on the total weight of the rivastigmine-containing layer;
2. a silicone acrylic hybrid polymer containing a continuous, silicone external phase and a discontinuous, acrylic internal phase, in an amount of from 45 to 90% by weight based on the total weight of the rivastigmine-containing layer; and
3. optionally a pressure-sensitive adhesive based on polysiloxanes in an amount of from 10 to 30% by weight based on the total weight of the rivastigmine-containing layer;
wherein said rivastigmine-containing layer is the skin contact layer;
and wherein the area weight of said rivastigmine-containing layer ranges from 60 to 180 g/m².

According to one specific aspect, the present invention relates to a transdermal therapeutic system for the transdermal administration of rivastigmine, comprising a rivastigmine-containing layer structure, said rivastigmine-containing layer structure comprising:
A) a backing layer; and
B) a rivastigmine-containing layer comprising:
1. rivastigmine in an amount of from 10 to 25% by weight based on the total weight of the rivastigmine-containing layer;
2. a silicone acrylic hybrid polymer containing a continuous, acrylic external phase and a discontinuous, silicone internal phase, in an amount of from 40 to 90% by weight based on the total weight of the rivastigmine-containing layer; and
3. optionally a pressure-sensitive adhesive based on acrylates in an amount of from 5 to 40% by weight based on the total weight of the rivastigmine-containing layer;
wherein said rivastigmine-containing layer is the skin contact layer;
and wherein the area weight of said rivastigmine-containing layer ranges from 60 to 180 g/m².

According to certain embodiments of the invention, the transdermal therapeutic system according to the invention is for use in a method of treating a human patient, preferably for use in a method of preventing, treating, or delaying of progression of Alzheimer's disease, dementia associated with Parkinson's disease, and/or symptoms of traumatic brain injury, or for use in a method of treating mild to moderate dementia caused by Alzheimer's or Parkinson's disease.

According to certain embodiments of the invention, the transdermal therapeutic system according to the invention is for a method of treating a human patient, in particular preventing, treating, or delaying of progression of Alzheimer's disease, dementia associated with Parkinson's disease, and/or symptoms of traumatic brain injury, or treating a mild to moderate dementia caused by Alzheimer's and Parkinson's disease by applying a transdermal therapeutic system according to the invention to the skin of the patient.

According to another aspect, the present invention relates to a process for manufacturing a rivastigmine-containing layer for use in a transdermal therapeutic system according to the invention comprising the steps of:
1) combining at least the components
  1. rivastigmine in an amount such that the amount of rivastigmine in the resulting rivastigmine-containing layer is from 10 to 25% by weight based on the total weight of the rivastigmine-containing layer;
  2. a silicone acrylic hybrid polymer, and
  3. optionally at least one additional non-hybrid polymer and/or additive, to obtain a coating composition;
2) coating the coating composition onto the backing layer or release liner; and
3) drying the coated coating composition to form the rivastigmine-containing layer, wherein preferably the silicone acrylic hybrid polymer is provided as a solution, wherein the solvent is ethyl acetate or n-heptane.

Definitions

Within the meaning of this invention, the term "transdermal therapeutic system" (TTS) refers to a system by which the active agent (e.g. rivastigmine) is administered to the systemic circulation via transdermal delivery and refers to the entire individual dosing unit that is applied, after removing an optionally present release liner, to the skin of a patient, and which comprises a therapeutically effective amount of active agent in an active agent-containing layer structure and optionally an additional adhesive overlay on top of the active agent-containing layer structure. The active agent-containing layer structure may be located on a release liner (a detachable protective layer), thus, the TTS may further comprise a release liner. Within the meaning of this invention, the term "TTS" in particular refers to systems providing transdermal delivery, excluding active delivery for example via iontophoresis or microporation. Transdermal therapeutic systems may also be referred to as transdermal drug delivery systems (TDDS) or transdermal delivery systems (TDS).

Within the meaning of this invention, the term "rivastigmine-containing layer structure" refers to the layer structure containing a therapeutically effective amount of rivastigmine and comprises a hacking layer and at least one active agent-containing layer. Preferably, the rivastigmine-containing layer structure is a rivastigmine-containing self-adhesive layer structure.

Within the meaning of this invention, the term "therapeutically effective amount" refers to a quantity of active agent in the TTS sufficient to provide, if administered by the TTS to a patient, prevents, treats, or delays of progression of Alzheimer's disease, dementia associated with Parkinson's disease, and/or symptoms of traumatic brain injury. A TTS usually contains more active in the system than is in fact provided to the skin and the systemic circulation. This excess amount of active agent is usually necessary to provide enough driving force for the delivery from the TTS to the systemic circulation.

Within the meaning of this invention, the terms "active", "active agent", and the like, as well as the term "rivastigmine" refer to rivastigmine in any pharmaceutically acceptable chemical and morphological form and physical state. These forms include without limitation rivastigmine in its free base/free acid form, protonated or partially protonated rivastigmine, rivastigmine salts, cocrystals and in particular acid/base addition salts formed by addition of an inorganic or organic acid/base such as rivastigmine hydrochloride or rivastigmine tartrate, solvates, hydrates, clathrates, complexes and so on, as well as rivastigmine in the form of particles which may be micronized, crystalline and/or amorphous, and any mixtures of the aforementioned forms. The rivastigmine, where contained in a medium such as a solvent, may be dissolved or dispersed or in part dissolved and in part dispersed.

When rivastigmine is mentioned to be used in a particular form in the manufacture of the TTS, this does not exclude interactions between this form of rivastigmine and other ingredients of the rivastigmine-containing layer structure, e.g. salt formation or complexation, in the final TTS. This means that, even if rivastigmine is included in its free base/acid form, it may be present in the final TTS in protonated or partially protonated/or deprotonated or partially deprotonated form or in the form of an acid addition salt, or, if it is included in the form of a salt, parts of it may be present as free base in the final TTS. Unless otherwise indicated, in particular the amount of rivastigmine in the layer structure relates to the amount of rivastigmine included in the TTS during manufacture of the TTS and is calculated based on rivastigmine in the form of the free base. E.g., when a) 0.1 mmol (equal to 25.03 mg) rivastigmine base or b) 0.1 mmol (equal to 40.04 mg) rivastigmine tartrate is included in the TTS during manufacture, the amount of rivastigmine in the layer structure is, within the meaning of the invention, in both cases 0.1 mmol or 25.03 mg.

The rivastigmine starting material included in the TTS during manufacture of the TTS may be in the form of particles. Rivastigmine may e.g. be present in the active agent-containing layer structure in the form of particles and/or dissolved.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. rivastigmine) is not totally dissolved. Dispersing in the sense of the invention comprises the dissolution of a part of the starting material (e.g. rivastigmine particles), depending on the solubility of the starting material (e.g. the solubility of rivastigmine in the coating composition).

There are two main types of TTS for active agent delivery, i.e. matrix-type TTS and reservoir-type TTS. The release of the active agent in a matrix-type TTS is mainly controlled by the matrix including the active agent itself. In contrast thereto, a reservoir-type TTS typically needs a rate-controlling membrane controlling the release of the active agent. In principle, also a matrix-type TTS may contain a rate-controlling membrane. However, matrix-type TTS are advantageous in that, compared to reservoir-type TTS, usually no rate determining membranes are necessary and no dose dumping can occur due to membrane rupture. In summary, matrix-type transdermal therapeutic systems (TTS) are less complex in manufacture and easy and convenient to use by patients.

Within the meaning of this invention, "matrix-type TTS" refers to a system or structure wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. Preferably, the matrix layer has sufficient cohesion to be self-supporting so that no sealing between other layers is required. Accordingly, the active agent-containing layer may in one embodiment of the invention be an active agent-containing matrix layer, wherein the active agent is homogeneously distributed within a polymer matrix. In certain embodiments, the active agent-containing matrix layer may comprise two active agent-containing matrix layers, which may be laminated together. Matrix-type TTS may in particular be in the form of a "drug-in-adhesive"-type TTS referring to a system wherein the active is homogeneously dissolved and/or dispersed within a pressure-sensitive adhesive matrix. In this connection, the active agent-containing matrix layer may also be referred to as active agent-containing pressure sensitive adhesive layer or active agent-containing pressure sensitive adhesive matrix layer. A TTS comprising the active agent dissolved and/or dispersed within a polymeric gel, e.g. a hydrogel, is also considered to be of matrix-type in accordance with present invention.

TTS with a liquid active agent-containing reservoir are referred to by the term "reservoir-type TTS". In such a system, the release of the active agent is preferably controlled by a rate-controlling membrane. In particular, the reservoir is sealed between the backing layer and the rate-controlling membrane. Accordingly, the active agent-containing layer may in one embodiment be an active agent-containing reservoir layer, which preferably comprises a liquid reservoir comprising the active agent. Furthermore, the reservoir-type TTS typically additionally comprises a skin contact layer, wherein the reservoir layer and the skin contact layer may be separated by the rate-controlling membrane. In the reservoir layer, the active agent is preferably dissolved in a solvent such as ethanol or water or in silicone oil. The skin contact layer typically has adhesive properties.

Reservoir-type TTS are not to be understood as being of matrix-type within the meaning of the invention. However, microreservoir TTS (biphasic systems having deposits (e.g. spheres, droplets) of an inner active-containing phase dispersed in an outer polymer phase), considered in the art to be a mixed from of a matrix-type TTS and a reservoir-type TTS that differ from a homogeneous single phase matrix-type TTS and a reservoir-type TTS in the concept of drug transport and drug delivery, are considered to be of matrix-type within the meaning of the invention. The sizes of microreservoir droplets can be determined by an optical microscopic measurement (for example by Leica MZ16 including a camera, for example Leica DSC320) by taking pictures of the microreservoirs at different positions at an enhancement factor between 10 and 400 times, depending on the required limit of detection. By using imaging analysis software, the sizes of the microreservoirs can be determined.

Within the meaning of this invention, the term "active agent-containing layer" refers to a layer containing the active agent and providing the area of release. The term covers active agent-containing matrix layers and active agent-containing reservoir layers. If the active agent-containing layer is an active agent-containing matrix layer, said layer is present in a matrix-type TTS. If the polymer is a pressure-sensitive adhesive, the matrix layer may also represent the adhesive layer of the TTS, so that no additional skin contact layer is present. Alternatively, an additional skin contact layer may be present as adhesive layer, and/or an adhesive overlay is provided. The additional skin contact layer is typically manufactured such that it is active agent-free. However, due to the concentration gradient, the active agent will migrate from the matrix layer to the additional skin contact layer over time, until an equilibrium is reached. The additional skin contact layer may be present on the active agent-containing matrix layer or separated from the active agent-containing matrix layer by a membrane, preferably a rate controlling membrane. Preferably, the active agent-containing matrix layer has sufficient adhesive properties, so that no additional skin contact layer is present. If the active agent-containing layer is an active agent-containing reservoir layer, said layer is present in a reservoir-type TTS, and the layer comprises the active agent in a liquid reservoir. In addition, an additional skin contact layer is preferably present, in order to provide adhesive properties. Preferably, a rate-controlling membrane separates the reservoir layer from the additional skin contact layer. The additional skin contact layer can be manufactured such that it is active agent-free or active agent-containing. If the additional skin contact layer is free of active agent the active agent will migrate, due to the concentration gradient, from the reservoir layer to the skin contact layer over time, until an equilibrium is reached. Additionally an adhesive overlay may be provided.

As used herein, the active agent-containing layer is preferably an active agent-containing matrix layer, and it is referred to the final solidified layer. Preferably, an active agent-containing matrix layer is obtained after coating and drying the solvent-containing coating composition as described herein. Alternatively an active-agent containing matrix layer is obtained after melt-coating and cooling. The active agent-containing matrix layer may also be manufactured by laminating two or more such solidified layers (e.g. dried or cooled layers) of the same composition to provide the desired area weight. The matrix layer may be self-adhesive (in the form of a pressure sensitive adhesive matrix layer), or the TTS may comprise an additional skin contact layer of a pressure sensitive adhesive for providing sufficient tack. Preferably, the matrix layer is a pressure sensitive adhesive matrix layer. Optionally, an adhesive overlay may be present.

Within the meaning of this invention, the term "pressure-sensitive adhesive" (also abbreviated as "PSA") refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix layer or in the form of an additional layer, i.e. a pressure sensitive adhesive skin contact layer. An adhesive overlay may still be employed to advance adhesion. The pressure-sensitive adhesive properties of a pressure-sensitive adhesive depend on the polymer or polymer composition used.

Within the meaning of this invention, the term "silicone acrylic hybrid polymer" refers to a polymerization product including repeating units of a silicone sub-species and an acrylate-sub species. The silicone acrylic hybrid polymer thus comprises a silicone phase and an acrylic phase. The term "silicone acrylic hybrid" is intended to denote more than a simple blend of a silicone-based sub-species and an acrylate-based sub-species. Instead, the term denotes a polymerized hybrid species that includes silicone-based sub-species and acrylate-based sub-species that have been polymerized together. The silicone acrylic hybrid polymer may also be referred to as a "silicone acrylate hybrid polymer" as the terms acrylate and acrylic are generally used interchangeably in the context of the hybrid polymers used in the present invention.

Within the meaning of this invention, the term "silicone acrylic hybrid pressure-sensitive adhesive" refers to a silicone acrylic hybrid polymer in the form of a pressure-sensitive adhesive. Silicone acrylic hybrid pressure-sensitive adhesives are described, for example, in EP 2 599 847 and WO 2016/130408. Examples of silicone acrylic hybrid pressure-sensitive adhesives include the PSA series 7-6100 and 7-6300 manufactured and supplied in n-heptane or ethyl acetate by Dow Corning (7-610X and 7-630X; X=1 n-heptane-based/X=2 ethyl acetate-based). It was found that, depending on the solvent in which the silicone acrylic hybrid PSA is supplied, the arrangement of the silicone phase and the acrylic phase providing a silicone or acrylic continuous external phase and a corresponding discontinuous internal phase is different. If the silicone acrylic hybrid PSA is supplied in n-heptane, the composition contains a continuous, silicone external phase and a discontinuous, acrylic internal phase. If the silicone acrylic hybrid PSA composition is supplied in ethyl acetate, the composition contains a continuous, acrylic external phase and a discontinuous, silicone internal phase.

Within the meaning of this invention, the term "non-hybrid polymer" is used synonymously for a polymer which does not include a hybrid species. Preferably, the non-hybrid polymer is a pressure-sensitive adhesive (e.g. a silicone- or acrylate-based pressure-sensitive adhesives).

Within the meaning of this invention, the term "silicon-containing pressure-sensitive adhesive composition comprising acrylate or methacrylate functionality" comprises the condensation reaction product of a silicone resin, a silicone polymer, and a silicon-containing capping agent which provides said acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

As used herein, an active agent-containing matrix layer is a layer containing the active agent dissolved or dispersed in at least one polymer, or containing the active agent dissolved in a solvent to for ii. an active agent-solvent mixture that is dispersed in the form of deposits (in particular droplets) in at least one polymer. Preferably, the at least one polymer is a polymer-based pressure-sensitive adhesive (e.g. a silicone acrylic hybrid pressure-sensitive adhesive). Within the meaning of this invention, the term "pressure-sensitive adhesive layer" refers to a pressure-sensitive adhesive layer obtained from a solvent-containing adhesive coating composition after coating on a film and evaporating the solvents.

Within the meaning of this invention, the term "skin contact layer" refers to the layer included in the active agent-containing layer structure to be in direct contact with the skin of the patient during administration. This may be the active agent-containing layer. When the TTS comprises an additional skin contact layer, the other layers of the active agent-containing layer structure do not contact the skin and do not necessarily have self-adhesive properties. As outlined above, an additional skin contact layer attached to the active agent-containing layer may over time absorb parts of the active agent. An additional skin contact layer may be used to enhance adherence. The sizes of an additional skin contact layer and the active agent-containing layer are usually coextensive and correspond to the area of release. However, the area of the additional skin contact layer may also be greater than the area of the active agent-containing layer. In such a case, the area of release still refers to the area of the active agent-containing layer.

Within the meaning of this invention, the term "area weight" refers to the dry weight of a specific layer, e.g. of the matrix layer, provided in $g/m^2$. The area weight values are subject to a tolerance of ±10%, preferably ±7.5%, due to manufacturing variability.

If not indicated otherwise "%" refers to weight-% (% by weight).

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2000, preferably above 5000 and more preferably above 10,000 Dalton. Correspondingly, compounds with a molecular weight below 2000, preferably below 5000 or more preferably below 10,000 Dalton are usually referred to as oligomers.

Within the meaning of this invention, the term "cross-linking agent" refers to a substance which is able to cross-link functional groups contained within the polymer.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer that may provide occlusive or non-occlusive properties and an adhesive layer. Preferably, the backing layer of the adhesive overlay provides non-occlusive properties.

Within the meaning of this invention, the term "backing layer" refers to a layer which supports the active agent-containing layer or forms the backing of the adhesive overlay. At least one backing layer in the TTS and usually the backing layer of the active agent-containing layer is substantially impermeable to the active agent contained in the layer during the period of storage and administration and thus prevents active loss or cross-contamination in accordance with regulatory requirements. Preferably, the backing layer is also occlusive, meaning substantially impermeable to water and water-vapor. Suitable materials for a backing layer include polyethylene terephthalate (PET), polyethylene (PE), ethylene vinyl acetate-copolymer (EVA), polyurethanes, and mixtures thereof. Suitable backing layers are thus for example PET laminates, EVA-PET laminates and PE-PET laminates. Also suitable are woven or non-woven backing materials.

The TTS according to the present invention can be characterized by certain parameters as measured in an in vitro skin permeation test.

In general, the in vitro permeation test is performed in a Franz diffusion cell, with EVA membrane (e.g. 9% vinyl acetate and 50 µm thickness, preferably provided by 3M), and with phosphate buffer pH 5.5 or 7.4 as receptor medium (32° C. with 0.1% saline azide).

Further, in vitro permeation test may be performed in a Franz diffusion cell, with human or animal skin and preferably with dermatomed split-thickness human skin with a thickness of 800 µm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylenglycol, PEG 400 so that a receptor medium may e.g. contain 60 vol-% phosphate buffer pH 5.5, 30 vol-% dipropylenglycol and 10 vol-% acetonitrile.

Where not otherwise indicated, the in vitro permeation test is performed with EVA membrane (9% vinyl acetate, 50 µm), and with phosphate buffer pH 5.5 as receptor medium (32° C. with 0.1% saline azide). The amount of active permeated into the receptor medium is determined in regular intervals using a validated HPLC method (column: stainless steel column 150 mm×4.6 mm internal diameter with C18 base and acid deactivated stationary phase, 3.5 µm particle size, e.g. Zorbax SB C18 (Agilent); column temperature: 25° C.; mobile phase: acetonitrile/water/TEA=20:80:0.35 (v/v/v) pH 3.5; flow rate: 1.0 ml/min; pressure: 135 bar; injection volume: 50 µL; stop time: 8 min) with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in $µg/cm^2$ and relates to the amount of active permeated in a sample interval at certain elapsed time. E.g., in an in vitro permeation test as described above, wherein the amount of active permeated into the receptor medium has been e.g. measured at hours 0, 2, 4, 8, 12 and 24, the "permeated amount" of active can be given e.g. for the sample interval from hour 8 to hour 12 and corresponds to the measurement at hour 12, wherein the receptor medium has been exchanged completely at hour 8.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in $µg/cm^2$-hr and is calculated from the permeated amount in said sample interval as measured by in vitro permeation test as described above in $µg/cm^2$, divided by the hours of said sample interval. E.g. the skin permeation rate in an in vitro permeation test as described above, wherein the amount of active permeated into the receptor medium has been e.g. measured at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters "permeated amount" and "skin permeation rate" (as well as "cumulative permeated amount" and "cumulative skin permeation rate") refer to mean values calculated from at least 3 in vitro permeation test experiments. Where not otherwise indicated, the standard deviation (SD) of these mean values refer to a corrected sample standard deviation, calculated using the formula:

$$SD = \sqrt{\frac{1}{n-1} \sum_{i=1}^{n} (x_i - \bar{x})^2}$$

wherein n is the sample size, $\{x_1, x_2, \ldots x_n\}$ are the observed values and $\bar{x}$ is the mean value of the observed values.

The TTS according to the present invention can also be characterized by certain parameters as measured in an in vivo clinical study.

Within the meaning of this invention, the parameter "mean release rate" refers to the mean release rate in µg/hr (µg/hour, µg/h) or in mg/day over the period of administration (e.g., 1 to 7 days) by which the active agent is released through the human skin into the systemic circulation and is based on the AUC obtained over said period of administration in a clinical study.

Within the meaning of this invention, the term "extended period of time" relates to a period of at least or about 24 hours, at least or about 48 hours, at least or about 84 hours, at least or about 168 hours, at least or about 1 day, at least or about 3.5 days, or at least or about 7 days, or to a period of about 24 hours to about 168 hours or 1 to 7 day(s), or about 24 hours to about 84 hours or 1 to 3.5 day(s).

For a continuous drug treatment, the frequency of drug administration is preferably kept sufficiently high so as to maintain therapeutically effective blood plasma concentration. In other words, the interval between two dosage form administrations, also called dosing interval, needs to be adapted accordingly. Within the meaning of the present invention, the term "dosing interval" refers to the period of time between two consecutive TTS administrations, i.e. the interval between two consecutive points in time a TTS is applied to the skin of the patient. Once applied, the TTS is usually maintained on the skin of the patient for the entire dosing interval and only removed at the end of the dosing interval, at which time a new TTS is applied to the skin. E.g., if the dosing interval is 24 hours or 1 day, the TTS is applied to and maintained on the skin of the patient for 24 hours or 1 day. After 24 hours or 1 day, the TTS is removed from the skin and a new TTS is applied. Thus, a dosing interval of 24 hours or 1 day allows a daily TTS exchange mode in an around-the-clock treatment.

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention the term "pharmacokinetic parameters" refers to parameters describing the blood plasma curve, e.g. $C_{max}$, $C_t$ and $AUC_{t1-t2}$ obtained in a clinical study, e.g. by single-dose, multi-dose or steady state administration of the active agent-containing TTS, e.g. the rivastigmine-containing TTS to healthy human subjects. The pharmacokinetic parameters of the individual subjects are summarized using arithmetic and geometric means, e.g. a mean $C_{max}$, a mean AUCt and a mean AUCINF, and additional statistics such as the respective standard deviations and standard errors, the minimum value, the maximum value, and the middle value when the list of values is ranked (Median). In the context of the present invention, pharmacokinetic parameters, e.g. the $C_{max}$, $C_t$ and $AUC_{t1-t2}$ refer to geometric mean values if not indicated otherwise. It cannot be precluded that the absolute mean values obtained for a certain TTS in a clinical study vary to a certain extent from study to study. To allow a comparison of absolute mean values between studies, a reference formulation, e.g. in the future any product based on the invention, may be used as internal standard. A comparison of the AUC per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29.4 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least five, preferably at least ten individual healthy human subjects.

Within the meaning of this invention, the term "geometric mean" refers to the mean of the log transformed data back-transformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "$AUC_{t1-t2}$" is provided in (ng/ml) hr and relates to the area under the plasma concentration-time curve from hour t1 to t2 and is calculated by the linear trapezoidal method, unless otherwise indicated. Other calculation methods are e.g. the logarithmic and linear log trapezoidal method.

Within the meaning of this invention, the parameter "$C_{max}$" is provided in (ng/ml) and relates to the maximum observed blood plasma concentration of the active agent.

Within the meaning of this invention, the parameter "$C_t$" is provided in (ng/ml) and relates to the blood plasma concentration of the active agent observed at hour t.

Within the meaning of this invention, the parameter "$t_{max}$" is provided in hr and relates to the time point at which the $C_{max}$ value is reached. In other words, $t_{max}$ is the time point of the maximum observed plasma concentration.

Within the meaning of this invention, the term "mean plasma concentration" is provided in (ng/ml) and is a mean of the individual plasma concentrations of active agent, e.g. rivastigmine, at each point in time.

Within the meaning of this invention, the term "coating composition" refers to a composition comprising all components of the matrix layer in a solvent, which may be coated onto the backing layer or release liner to form the matrix layer upon drying.

Within the meaning of this invention, the term "pressure sensitive adhesive composition" refers to a pressure sensitive adhesive at least in mixture with a solvent (e.g. n-heptane or ethyl acetate).

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, toluene and mixtures thereof.

DETAILED DESCRIPTION

TTS Structure

Figure 1:
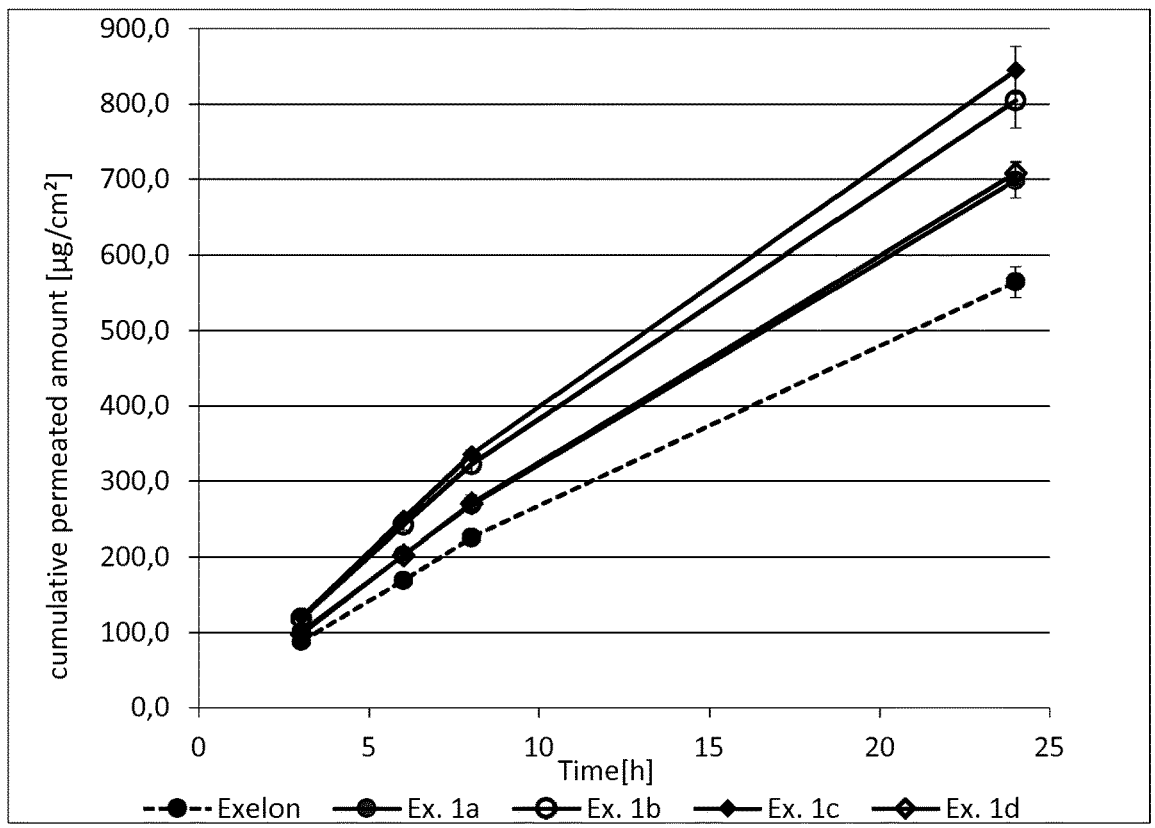
FIG. 1 depicts the rivastigmine cumulative permeated amount of TTS prepared according to Examples 1a-d and Exelon.

The present invention relates to a transdermal therapeutic system for the transdermal administration of rivastigmine comprising a rivastigmine-containing layer structure, said rivastigmine-containing layer structure comprising a) a backing layer, and b) a rivastigmine-containing layer, wherein the transdermal therapeutic system comprises a silicone acrylic hybrid polymer. This rivastigmine-containing layer structure is preferably a rivastigmine-containing self-adhesive layer structure and preferably does not comprise an additional skin contact layer. In particular, the silicone acrylic hybrid polymer, which is present in the transdermal therapeutic system, is present in the self-adhesive layer structure and provides the adhesive properties.

The TTS according to the present invention may be a matrix-type TTS or a reservoir-type TTS, and preferably is a matrix-type TTS.

In a matrix-type TTS according to the invention, the rivastigmine is homogeneously dissolved and/or dispersed within a polymeric carrier, i.e. the matrix, which forms with the rivastigmine and optionally remaining ingredients a matrix layer. Accordingly, the rivastigmine-containing layer may in one embodiment of the invention be a rivastigmine-containing matrix layer, wherein the rivastigmine is homogeneously distributed within a polymer matrix. The polymer matrix preferably comprises the silicone acrylic hybrid polymer. Thus, it is preferred according to the invention that the rivastigmine-containing matrix layer comprises rivastigmine and the silicone acrylic hybrid polymer, which is present in the TTS. In this connection, it is also preferred that the rivastigmine-containing matrix layer is self-adhesive, so that no additional skin contact layer is present. If a rivastigmine-containing matrix layer is prepared by laminating together two rivastigmine-containing matrix layers, which are of substantially the same composition, the resulting double layer is to be regarded as one rivastigmine-containing matrix layer.

In a reservoir-type TTS according to the present invention, the rivastigmine-containing layer is a rivastigmine-containing reservoir layer, which preferably comprises a liquid reservoir comprising the rivastigmine. The reservoir-type TTS typically additionally comprises a skin contact layer, wherein the reservoir layer and the skin contact layer are preferably separated by the rate-controlling membrane. The silicone acrylic hybrid polymer then provides the adhesive properties. Preferably, the skin contact layer is manufactured such that it is rivastigmine-free.

In a preferred embodiment of the invention, the rivastigmine-containing layer is a rivastigmine-containing matrix layer comprising
1. rivastigmine, and
2. the silicone acrylic hybrid polymer.

Thus, according to one embodiment of the invention, the transdermal therapeutic system for the transdermal administration of rivastigmine comprises a rivastigmine-containing layer structure comprising:
A) a backing layer; and
B) a rivastigmine-containing layer, which is preferably a rivastigmine-containing matrix layer, comprising:
   1. rivastigmine, and
   2. a silicone acrylic hybrid polymer.

The rivastigmine-containing layer structure is preferably a rivastigmine-containing self-adhesive layer structure. In this connection, it is also preferred that the rivastigmine-containing layer structure does not comprise an additional skin contact layer. Instead, it is preferred that the rivastigmine-containing layer, which is preferably a rivastigmine-containing matrix layer, is self-adhesive. Thus, in a preferred embodiment, the rivastigmine-containing layer structure is a rivastigmine-containing self-adhesive layer structure and does not comprise an additional skin contact layer. Alternatively or additionally, it is preferred that the rivastigmine-containing layer is directly attached to the backing layer, so that there is no additional layer between the backing layer and the rivastigmine-containing layer. Consequently, a layer structure of low complexity is obtained, which is advantageous, e.g., in terms of the costs for the manufacture.

In particular, it is preferred that the rivastigmine-containing layer structure comprises not more than 3, preferably 2 layers, i.e. preferably only the backing layer and the rivastigmine-containing layer. Sufficient adhesion between the rivastigmine-containing self-adhesive layer structure and the skin of the patient during administration is then provided by the rivastigmine-containing layer, which is preferably a rivastigmine-containing matrix layer. If an additional skin contact layer is present, e.g., as the third layer of the rivastigmine-containing layer structure, the adhesive properties may be provided by the additional skin contact layer. However, it is preferred according to the invention that no additional skin contact layer is present.

The self-adhesive properties of the rivastigmine-containing layer structure are preferably provided by the silicone acrylic hybrid polymer, which is present in the TTS, preferably in the rivastigmine-containing layer, more preferably in the rivastigmine-containing matrix layer. Thus, in a preferred embodiment of the invention, the silicone acrylic hybrid polymer is a silicone acrylic hybrid pressure sensitive adhesive. Further details regarding the silicone acrylic hybrid polymer according to the invention are provided further below.

It is to be understood that the TTS according to the invention contains a therapeutically effective amount of rivastigmine. Thus, in a preferred embodiment of the invention, the rivastigmine-containing layer structure contains a therapeutically effective amount of rivastigmine. The rivastigmine in the rivastigmine-containing layer structure is preferably present in the form of the free base. Preferred embodiments regarding the rivastigmine in the TTS according to the invention are provided further below.

It is preferred according to the invention that the area of release of the TTS is rather small. According to one specific embodiment of the invention, the area of release ranges from 1 to 30 cm$^2$, preferably from 2 to 22 cm$^2$.

In a preferred embodiment of the invention, the backing layer is substantially rivastigmine impermeable. Furthermore, it is preferred that the backing layer is occlusive as outlined above.

According to certain embodiments of the invention, the TTS may further comprise an adhesive overlay. This adhesive overlay is in particular larger in area than the rivastigmine-containing structure and is attached thereto for enhancing the adhesive properties of the overall transdermal therapeutic system. Said adhesive overlay comprises a backing layer and an adhesive layer. The adhesive overlay provides additional area adhering to the skin but does not add to the area of release of the rivastigmine. The adhesive overlay comprises a self-adhesive polymer or a self-adhesive polymer mixture selected from the group consisting of silicone acrylic hybrid polymers, acrylic polymers, polysiloxanes, polyisobutylenes, styrene-isoprene-styrene copolymers, and mixtures thereof, which may be identical to or different from any polymer or polymer mixture included in the rivastigmine-containing layer structure.

The rivastigmine-containing layer structure according to the invention, such as a rivastigmine-containing self-adhesive layer structure, is normally located on a detachable protective layer (release liner), from which it is removed immediately before application to the surface of the patient's skin. Thus, the TTS may further comprise a release liner. A TTS protected this way is usually stored in a blister pack or a seam-sealed pouch. The packaging may be child resistant and/or senior friendly.

Rivastigmine-Containing Layer

As outlined in more detail above, the TTS according to the present invention comprises a rivastigmine-containing layer structure comprising a rivastigmine-containing layer. Preferably, the rivastigmine-containing layer structure is a rivastigmine-containing self-adhesive layer structure. Accordingly, it is also preferred that the rivastigmine-containing layer is a self-adhesive rivastigmine-containing layer, more preferably a self-adhesive rivastigmine-containing matrix layer. In a preferred embodiment, the rivastigmine-containing layer comprises a therapeutically affective amount of the rivastigmine.

In one embodiment of the invention, the rivastigmine-containing layer is a rivastigmine-containing matrix layer. In another embodiment, the rivastigmine-containing layer is a rivastigmine-containing reservoir layer. It is preferred that the rivastigmine-containing layer is a rivastigmine-containing matrix layer.

In one embodiment, the rivastigmine-containing layer comprises:
1. rivastigmine, preferably in the form of the free base; and
2. a silicone acrylic hybrid polymer.

In a preferred embodiment, the rivastigmine-containing layer is a rivastigmine-containing matrix layer comprising
1. rivastigmine, preferably in the form of the free base; and
2. a silicone acrylic hybrid polymer.

In a preferred embodiment, the invention relates to a rivastigmine-containing layer structure, wherein the silicone acrylic hybrid polymer is a silicone acrylic hybrid pressure-sensitive adhesive.

In one embodiment of the invention, the rivastigmine-containing layer is obtainable by dissolving, dispersing, or partly dissolving and partly dispersing the rivastigmine, preferably in the form of the free base. As a result, the rivastigmine-containing layer of the TTS according to the invention typically comprises rivastigmine in the form of the free base. In addition, the rivastigmine may, in certain embodiments of the invention, partly be present in protonated form. However, it is preferred that at least 50 mol %, preferably at least 75 mol % of the rivastigmine in the rivastigmine-containing layer are present in the form of the free base. In a particular preferred embodiment, at least 90 mol %, preferably at least 95 mol %, more preferably at least 99 mol % of the rivastigmine in the rivastigmine-containing layer are present in the form of the free base.

In one embodiment of the invention, the amount of rivastigmine contained in the rivastigmine-containing layer structure ranges from 0.5 to 5 mg/cm$^2$, preferably from 1 to 3 mg/cm$^2$. The total amount of rivastigmine in the rivastigmine-containing layer structure ranges from 1 to 45, preferably from 3 to 40 mg/TTS.

In one embodiment of the invention, the rivastigmine-containing layer comprises rivastigmine in an amount of from 5 to 30% by weight, preferably from 7 to 28% by weight, most preferably from 10 to 25% by weight, based on the total weight of the rivastigmine-containing layer.

In one embodiment of to the invention, the silicone acrylic hybrid polymer in the rivastigmine-containing layer contains a continuous, silicone external phase and a discontinuous, acrylic internal phase, or a continuous, acrylic external phase and a discontinuous, silicone internal phase, and wherein preferably the rivastigmine is present in the rivastigmine-containing layer in an amount of from 15 to 25% by weight based on the total weight of the rivastigmine-containing layer.

In one embodiment, the rivastigmine-containing layer structure is a rivastigmine-containing self-adhesive layer structure and does not comprise an additional skin contact layer. In yet another embodiment, the silicone acrylic hybrid polymer is a silicon acrylic hybrid pressure-sensitive adhesive. When no additional skin contact layer is needed, the rivastigmine-containing layer is preferably a rivastigmine-containing matrix layer, which has adhesive properties. The rivastigmine-containing matrix layer composition may comprise a second polymer or may comprise two or more further polymers.

In one embodiment of the invention, the amount of the silicone acrylic hybrid polymer ranges from 35 to 95% by weight, preferably from 40 to 93% by weight or from 45 to 90% by weight, based on the total weight of the rivastigmine-containing layer.

It is to be understood that the TTS according to the present invention may also comprise one or more non-hybrid polymers (e.g. non-hybrid pressure-sensitive adhesives) in addition to the silicone acrylic hybrid polymer. Exemplarily, non-hybrid polymers (e.g. non-hybrid pressure-sensitive adhesives) based on polysiloxanes, acrylates, polyisobutylenes, or styrene-isoprene-styrene block copolymers may be used. In one embodiment of the invention, the non-hybrid polymer is a pressure-sensitive adhesive based on polysiloxanes, acrylates, or polyisobutylene, in particular based on polysiloxanes or acrylates. Additional polymers may also be added to enhance cohesion and/or adhesion. In yet another preferred embodiment, the invention relates to a transdermal therapeutic system, wherein the rivastigmine-containing layer does not comprise a permeation enhancer or solubilizer.

In certain embodiments of the invention, the non-hybrid polymer is contained in the rivastigmine-containing layer in an amount of from 5 to 40%, preferably from 8 to 35% by weight based on the total weight of the rivastigmine-containing layer. In another embodiment of the invention, the weight ratio of the silicone acrylic hybrid polymer to the non-hybrid polymer is from 8:1 to 1:2, preferably from 7:1 to 1:1.

In one embodiment of the invention, the area weight of the rivastigmine-containing layer ranges from 40 to 250 g/m$^2$, preferably from 50 to 200 g/m$^2$. In certain preferred embodiments, the area weight ranges from 60 to 180 g/m$^2$.

In certain embodiments of the invention, the TTS for the transdermal administration of rivastigmine comprises a rivastigmine-containing layer structure, said rivastigmine-containing layer structure comprising:
A) a backing layer; and
B) a rivastigmine-containing layer comprising:
 1. rivastigmine in an amount of from 10 to 25% by weight based on the total weight of the rivastigmine-containing layer;
 2. a silicone acrylic hybrid polymer containing a continuous, silicone external phase and a discontinuous, acrylic internal phase, in an amount of from 45 to 90% by weight based on the total weight of the rivastigmine-containing layer; and
 3. optionally a pressure-sensitive adhesive based on polysiloxanes in an amount of from 10 to 30% by weight based on the total weight of the rivastigmine-containing layer;
wherein said rivastigmine-containing layer is the skin contact layer;
and wherein the area weight of said rivastigmine-containing layer ranges from 60 to 180 g/m$^2$.

In certain embodiments of the invention, the TTS for the transdermal administration of rivastigmine comprising a rivastigmine-containing layer structure, said rivastigmine-containing layer structure comprising:

A) a backing layer; and
B) a rivastigmine-containing layer comprising:
 1. rivastigmine in an amount of from 10 to 25% by weight based on the total weight of the rivastigmine-containing layer;
 2. a silicone acrylic hybrid polymer containing a continuous, acrylic external phase and a discontinuous, silicone internal phase, in an amount of from 40 to 90% by weight based on the total weight of the rivastigmine-containing layer; and
 3. optionally a pressure-sensitive adhesive based on acrylates in an amount of from 5 to 40% by weight based on the total weight of the rivastigmine-containing layer;
wherein said rivastigmine-containing layer is the skin contact layer;
and wherein the area weight of said rivastigmine-containing layer ranges from 60 to 180 g/m$^2$.

Rivastigmine

The TTS according to the invention comprises a rivastigmine-containing layer structure, said rivastigmine containing layer structure comprising A) a backing layer; and B) a rivastigmine containing layer; wherein the transdermal therapeutic system comprises a silicone acrylic hybrid polymer.

In one embodiment of the invention, the amount of rivastigmine contained in the rivastigmine-containing layer structure ranges from 0.5 to 5 mg/cm$^2$, preferably from 1 to 3 mg/cm$^2$.

In one embodiment of the invention, the rivastigmine-containing layer structure preferably contains a therapeutically effective amount of rivastigmine. More preferably, the therapeutically effective amount of rivastigmine is present in the rivastigmine-containing layer of the rivastigmine-containing layer structure. Preferably, the rivastigmine in the rivastigmine-containing layer structure is present in the form of the free base.

In one embodiment of the invention, at least 50 mol %, preferably at least 75 mol % of the total amount of rivastigmine in the TTS are present in the form of the free base. In a particular preferred embodiment, at least 90 mol %, preferably at least 95 mol %, more preferably at least 99 mol % of the total amount of rivastigmine in the TTS are present in the form of the free base. Thus, it is preferred that at least 50 mol %, preferably at least 75 mol % of the rivastigmine in the rivastigmine-containing layer are present in the form of the free base. In a particular preferred embodiment, at least 90 mol %, preferably at least 95 mol %, more preferably at least 99 mol % of the rivastigmine in the rivastigmine-containing layer are present in the form of the free base. In certain embodiments, the rivastigmine-containing layer is free of rivastigmine salts.

In certain embodiments, the amount of rivastigmine in the rivastigmine-containing layer ranges from 5 to 30% by weight, preferably from 7 to 28% by weight, most preferably from 10 to 25% by weight, based on the total weight of the rivastigmine-containing layer.

In certain embodiments, the amount of rivastigmine contained in the rivastigmine-containing layer ranges from 1 to 45 mg, preferably from 3 to 40 mg/TTS, depending on the patch size. In a patch of the size of e.g. 5 cm$^2$, the amount of rivastigmine contained in the rivastigmine-containing layer ranges from 5 to 15 mg, preferably from 7 to 12 mg.

In one embodiment of the invention, the rivastigmine-containing layer is obtainable by dissolving or dispersing the rivastigmine in the form of the free base. If the rivastigmine-containing layer is a rivastigmine-containing matrix layer, said layer is preferably obtainable by dissolving or dispersing the rivastigmine in the form of the free base in the polymeric carrier, which particularly preferably comprises the silicone acrylic hybrid polymer.

In one embodiment, the rivastigmine-containing layer comprises a pharmaceutically acceptable salt of rivastigmine, such as rivastigmine hydrochloride or rivastigmine tartrate, preferably rivastigmine tartrate. However, it is preferred according to the invention that the rivastigmine in the rivastigmine-containing layer is present in the form of the free base.

In certain embodiments, the rivastigmine has a purity of at least 95%, preferably of at least 98%, and more preferably of at least 99% as determined by quantitative HPLC. Quantitative HPLC may be performed with Reversed-Phase-HPLC with UV detection.

Silicone Acrylic Hybrid Polymer

The TTS according to the present invention comprises a silicone acrylic hybrid polymer. The silicone acrylic hybrid polymer comprises a polymerized hybrid species that includes silicone-based sub-species and acrylate-based sub-species that have been polymerized together. The silicone acrylic hybrid polymer thus comprises a silicone phase and an acrylic phase. Preferably, the silicone acrylic hybrid polymer is a silicone acrylic hybrid pressure-sensitive adhesive.

The silicone acrylic hybrid pressure-sensitive adhesives are usually supplied and used in solvents like n-heptane and ethyl acetate. The solids content of the pressure-sensitive adhesives is usually between 30% and 80%. The skilled person is aware that the solids content may be modified by adding a suitable amount of solvent.

Preferably, the weight ratio of silicone to acrylate in the silicone acrylic hybrid pressure-sensitive adhesive is from 5:95 to 95:5, or from 20:80 to 80:20, more preferably from 40:60 to 60:40, and most preferably the ratio of silicone to acrylate is about 50:50. Suitable silicone acrylic hybrid pressure-sensitive adhesives having a weight ratio of silicone to acrylate of 50:50 are, for example, the commercially available silicone acrylic hybrid pressure-sensitive adhesives 7-6102, Silicone/Acrylate Ratio 50/50, and 7-6302, Silicone/Acrylate Ratio 50/50, supplied in ethyl acetate by Dow Corning.

The preferred silicone acrylic hybrid pressure-sensitive adhesives in accordance with the invention are characterized by a solution viscosity at 25° C. and about 50% solids content in ethyl acetate of more than about 400 cP, or from about 500 cP to about 3,500 cP, in particular from about 1,000 cP to about 3,000 cP, more preferred from about 1,200 cP to about 1,800, or most preferred of about 1,500 cP or alternatively more preferred from about 2,200 cP to about 2,800 cP, or most preferred of about 2,500 cP, preferably as measured using a Brookfield RVT viscometer equipped with a spindle number 5 at 50 RPM.

These silicone acrylic hybrid pressure-sensitive adhesives may also be characterized by a complex viscosity at 0.1 rad/s at 30° C. of less than about 1.0e9 Poise, or from about 1.0e5 Poise to about 9.0e8 Poise, or more preferred from about 9.0e5 Poise to about 1.0e7 Poise, or most preferred about 4.0e6 Poise, or alternatively more preferred from about 2.0e6 Poise to about 9.0e7 Poise, or most preferred about 1.0e7 Poise, preferably as measured using a Rheometrics ARES rheometer, wherein the rheometer is equipped with 8 mm plates and the gap zeroed.

To prepare samples for measuring the rheological behavior using a Rheometrics ARES rheometer, between 2 and 3 grams of adhesive solution can be poured onto a SCOTCH-PAK 1022 fluoropolymer release liner and allow to sit for 60 minutes under ambient conditions. To achieve essentially solvent-free films of the adhesive, they can be placed in an oven at 110° C.+/−10° C. for 60 minutes. After removing from the oven and letting equilibrate to room temperature. The films can be removed from the release liner and folded over to form a square. To eliminate air bubbles the films can be compressed using a Carver press. The samples can then be loaded between the plates and are compressed to 1.5+/−0.1 mm at 30° C. The excess adhesive is trimmed and the final gap recorded. A frequency sweep between 0.01 to 100 rad/s can be performed with the following settings: Temperature=30° C.; strain=0.5-1% and data collected at 3 points/decade.

Suitable silicone acrylic hybrid pressure-sensitive adhesives which are commercially available include the PSA series 7-6100 and 7-6300 manufactured and supplied in n-heptane or ethyl acetate by Dow Corning (7-610X and 7-630X; X=1 n-heptane-based/X=2 ethyl acetate-based). For example, the 7-6102 silicone acrylic hybrid PSA having a silicone/acrylate ratio of 50/50 is characterized by a solution viscosity at 25° C. and about 50% solids content in ethyl acetate of 2,500 cP and a complex viscosity at 0.1 rad/s at 30° C. of 1.0e7 Poise. The 7-6302 silicone acrylic hybrid PSA having a silicone/acrylate ratio of 50/50 has a solution viscosity at 25° C. and about 50% solids content in ethyl acetate of 1,500 cP and a complex viscosity at 0.1 rad/s at 30° C. of 4.0e6 Poise.

Depending on the solvent in which the silicone acrylic hybrid pressure-sensitive adhesive is supplied, the arrangement of the silicone phase and the acrylic phase providing a silicone or acrylic continuous external phase and a corresponding discontinuous internal phase is different. If the silicone acrylic hybrid pressure-sensitive adhesive is provided in n-heptane, the composition contains a continuous, silicone external phase and a discontinuous, acrylic internal phase. If the silicone acrylic hybrid pressure-sensitive adhesive is provided in ethyl acetate, the composition contains a continuous, acrylic external phase and a discontinuous, silicone internal phase. After evaporating the solvent in which the silicone acrylic hybrid pressure-sensitive adhesive is provided, the phase arrangement of the resulting pressure-sensitive adhesive film or layer corresponds to the phase arrangement of the solvent-containing adhesive coating composition. For example, in the absence of any substance that may induce an inversion of the phase arrangement in a silicone acrylic hybrid pressure sensitive adhesive composition, a pressure-sensitive adhesive layer prepared from a silicone acrylic hybrid pressure-sensitive adhesive in n-heptane provides a continuous, silicone external phase and a discontinuous, acrylic internal phase, a pressure-sensitive adhesive layer prepared from a silicone acrylic hybrid pressure-sensitive adhesive in ethyl acetate provides a continuous, acrylic external phase and a discontinuous, silicone internal phase. The phase arrangement of the compositions can, for example, be determined in peel force tests with pressure-sensitive adhesive films or layers prepared from the silicone acrylic hybrid PSA compositions which are attached to a siliconized release liner. The pressure-sensitive adhesive film contains a continuous, silicone external phase if the siliconized release liner cannot or can only hardly be removed from the pressure-sensitive adhesive film (laminated to a backing film) due to the blocking of the two silicone surfaces. Blocking results from the adherence of two silicone layers which comprise a similar surface energy. The silicone adhesive shows a good spreading on the siliconized liner and therefore can create a good adhesion to the liner. If the siliconized release liner can easily be removed the pressure-sensitive adhesive film contains a continuous, acrylic external phase. The acrylic adhesive has no good spreading due to the different surface energies and thus has a low or almost no adhesion to the siliconized liner.

According to a preferred embodiment of the invention the silicone acrylic hybrid polymer is a silicone acrylic hybrid pressure-sensitive adhesive obtainable from a silicon-containing pressure-sensitive adhesive composition comprising acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

According to certain embodiments of the invention the silicone acrylic hybrid pressure-sensitive adhesive comprises the reaction product of (a) a silicon-containing pressure-sensitive adhesive composition comprising acrylate or methacrylate functionality, (b) an ethylenically unsaturated monomer, and (c) an initiator. That is, the silicone acrylic hybrid pressure-sensitive adhesive is the product of the chemical reaction between these reactants ((a), (b), and (c)). In particular, the silicone acrylic hybrid pressure-sensitive adhesive includes the reaction product of (a) a silicon-containing pressure-sensitive adhesive composition comprising acrylate or methacrylate functionality, (b) a (meth) acrylate monomer, and (c) an initiator (i.e., in the presence of the initiator). That is, the silicone acrylic hybrid pressure-sensitive adhesive includes the product of the chemical reaction between these reactants ((a), (b), and (c)).

The reaction product of (a) a silicon-containing pressure-sensitive adhesive composition comprising acrylate or methacrylate functionality, (b) an ethylenically unsaturated monomer, and (c) an initiator may contain a continuous, silicone external phase and a discontinuous, acrylic internal phase or the reaction product of (a), (b), and (c) may contain a continuous, acrylic external phase and a discontinuous, silicone internal phase.

The silicon-containing pressure-sensitive adhesive composition comprising acrylate or methacrylate functionality (a) is typically present in the silicone acrylic hybrid pressure-sensitive adhesive in an amount of from 5 to 95, more typically 25 to 75, parts by weight based on 100 parts by weight of the hybrid pressure-sensitive adhesive.

The ethylenically unsaturated monomer (b) is typically present in the silicone acrylic hybrid pressure-sensitive adhesive in an amount of from 5 to 95, more typically 25 to 75, parts by weight based on 100 parts by weight of the hybrid pressure-sensitive adhesive.

The initiator (c) is typically present in the silicone acrylic hybrid pressure-sensitive adhesive in an amount of from 0.005 to 3, more typically from 0.01 to 2, parts by weight based on 100 parts by weight of the hybrid pressure-sensitive adhesive.

According to certain embodiments of the invention the silicon-containing pressure-sensitive adhesive composition comprising acrylate or methacrylate functionality (a) comprises the condensation reaction product of (a1) a silicone resin, (a2) a silicone polymer, and (a3) a silicon-containing capping agent which provides said acrylate or methacrylate functionality. The silicone resin (a1) may also be referred to as silicate resin or silica resin. Preferably, the silicone polymer (a2) is a polysiloxane, preferably polydimethylsiloxane. It is to be understood that (a1) and (a2) form a silicone-based pressure sensitive adhesive by polycondensation, and that the acrylate or methacrylate functionality is introduced by reaction with (a3).

According to certain embodiments of the invention the silicon-containing pressure-sensitive adhesive composition comprising acrylate or methacrylate functionality (a) comprises the condensation reaction product of:
  (a1) a silicone resin,
  (a2) a silicone polymer, and
  (a3) a silicon-containing capping agent which provides said acrylate or methacrylate functionality, wherein said silicon-containing capping agent is of the general formula $XYR'_bSiZ_{3-b}$, wherein
    X is a monovalent radical of the general formula AE— where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure-sensitive adhesive, wherein the silicon-containing capping agent is introduced prior to, during, or after the silicone resin and silicone polymer are reacted, and wherein:
    the silicon-containing capping agent reacts with the pressure-sensitive adhesive after the silicone resin and silicone polymer have been condensation reacted to form the pressure-sensitive adhesive; or
    the silicon-containing capping agent reacts in-situ with the silicone resin and silicone polymer.

According to certain embodiments of the invention the silicon-containing pressure-sensitive adhesive composition comprising acrylate or methacrylate functionality comprises the condensation reaction product of a pressure sensitive adhesive and a silicon-containing capping agent which provides said acrylate or methacrylate functionality. That is, the silicon-containing pressure sensitive adhesive composition comprising acrylate or methacrylate functionality is essentially a pressure sensitive adhesive that has been capped or end blocked with the silicon-containing capping agent which provides said acrylate or methacrylate functionality, wherein the pressure sensitive adhesive comprises the condensation reaction product of the silicone resin and the silicone polymer. Preferably, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst. A wide array of silicone resins and silicone polymers are suitable to make up the pressure sensitive adhesive.

According to certain embodiments of the invention the silicone acrylic hybrid pressure-sensitive adhesive is the reaction product of:
(a) a silicon-containing pressure-sensitive adhesive composition comprising acrylate or methacrylate functionality that comprises the condensation reaction product of:
  (a1) a silicone resin,
  (a2) a silicone polymer, and
  (a3) a silicon-containing capping agent which provides said acrylate or methacrylate functionality, wherein said silicon-containing capping agent is of the general formula $XYR'_bSiZ_{3-b}$, wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer;
(b) an ethylenically unsaturated monomer; and
(c) an initiator.

The silicone acrylic hybrid composition used in the present invention may be described by being prepared by a method comprising the steps of:
(i) providing a silicon-containing pressure-sensitive adhesive composition comprising acrylate or methacrylate functionality that comprises the condensation reaction product of:
a silicone resin,
a silicone polymer, and
a silicon-containing capping agent which provides said acrylate or methacrylate functionality, wherein said silicon-containing capping agent is of the general formula $XYR'_bSiZ_{3-b}$, wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in the presence of an initiator to form a silicone acrylic hybrid composition, optionally at a temperature of from 50° C. to 100° C., or from 65° C. to 90° C.

During the polymerization of the ethylenically unsaturated monomer and the silicon-containing pressure-sensitive adhesive composition comprising acrylate or methacrylate functionality, the silicone to acrylic ratio can be controlled and optimized as desired. The silicone to acrylic ratio can be controlled by a wide variety of mechanisms in and during the method. An illustrative example of one such mechanism is the rate controlled addition of the ethylenically unsaturated monomer or monomers to the silicon-containing pressure-sensitive adhesive composition comprising acrylate or methacrylate functionality. In certain applications, it may be desirable to have the silicone-based sub-species, or the overall silicone content, to exceed the acrylate-based sub-species, or the overall acrylic content. In other applications, it may be desirable for the opposite to be true. Independent of the end application, it is generally preferred, as already described above, that the silicon-containing pressure-sensitive adhesive composition comprising acrylate or methacrylate functionality is preferably present in the silicone acrylic hybrid composition in an amount of from about 5 to about 95 parts by weight, more preferably from about 25 to about 75 parts by weight, and still more preferably from about 40 to about 60 parts by weight based on 100 parts by weight of the silicone acrylic hybrid composition.

According to a certain embodiment of the invention, the silicone acrylic hybrid composition used in the present invention may be described by being prepared by a method comprising the steps of:
(i) providing a silicon-containing pressure-sensitive adhesive composition comprising acrylate or methacrylate functionality that comprises the condensation reaction product of:
a silicone resin,
a silicone polymer, and
a silicon-containing capping agent which provides said acrylate or methacrylate functionality, wherein said silicon-containing capping agent is of the general formula $XYR'_bSiZ_{3-b}$, wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.

The silicone acrylic hybrid PSA composition used in the present invention may also be described by being prepared by a method comprising the steps of:
(i) providing a silicon-containing pressure-sensitive adhesive composition comprising acrylate or methacrylate functionality that comprises the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE— where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure-sensitive adhesive, wherein the silicon-containing capping agent is introduced prior to, during, or after the silicone resin and silicone polymer are reacted, and wherein:
    the silicon-containing capping agent reacts with the pressure-sensitive adhesive after the silicone resin and silicone polymer have been condensation reacted to form the pressure-sensitive adhesive; or
    the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) adding a processing solvent, wherein the processing solvent has a higher boiling point than the first solvent, and
(iv) applying heat at a temperature of from 70° C. to 150° C. such that a majority of the first solvent is selectively removed;
(v) removing the processing solvent; and.
(vi) adding a second solvent to form the silicone acrylic hybrid composition, wherein the phase arrangement of the silicone acrylic hybrid composition is selectively controlled by selection of the second solvent.

The silicone resin according to the previous paragraphs may contain a copolymer comprising triorganosiloxy units of the formula $R^X_3SiO_{1/2}$ and tetrafunctional siloxy units of the formula $SiO_{4/2}$ in a ratio of from 0.1 to 0.9, preferably of about 0.6 to 0.9, triorganosiloxy units for each tetrafunctional siloxy unit. Preferably, each $R^X$ independently denotes a monovalent hydrocarbon radical having from 1 to 6 carbon atoms, vinyl, hydroxyl or phenyl groups.

The silicone polymer according to the previous paragraphs may comprise at least one polydiorganosiloxane and is preferably end-capped (end-blocked) with a functional group selected from the group consisting of hydroxyl groups, alkoxy groups, hydride groups, vinyl groups, or mixtures thereof. The diorganosubstituent may be selected from the group consisting of dimethyl, methylvinyl, methylphenyl, diphenyl, methylethyl, (3,3,3-trifluoropropyl) methyl and mixtures thereof. Preferably, the diorganosubstituents contain only methyl groups. The molecular weight of polydiorganosiloxane will typically range from about 50,000 to about 1,000,000, preferably, from about 80,000 to about 300,000. Preferably, the polydiorganosiloxane comprises $AR^XSiO$ units terminated with endblocking $TR^XA\text{-}SiO_{1/2}$ units, wherein the polydiorganosiloxane has a viscosity of from about 100 centipoise to about 30,000,000 centipoise at 25° C., each A radical is independently selected from $R^X$ or halohydrocarbon radicals having from 1 to 6 carbon atoms, each T radical is independently selected from the group consisting of $R^X$, OH, H or $OR^Y$, and each $R^Y$ is independently an alkyl radical having from 1 to 4 carbon atoms.

As an example using forms of the preferred silicone resin and the preferred silicone polymer, one type of pressure sensitive adhesive is made by:
mixing (1) from 30 to 80 inclusive parts by weight of at least one resin copolymer containing silicon-bonded hydroxyl radicals and consisting essentially of $R^X_3SiO_{1/2}$ units and $SiO_{4/2}$ units in a mole ratio of 0.6 to 0.9 $R^X_3SiO_{1/2}$ units for each $SiO_{4/2}$ unit present, (ii) between about 20 and about 70 parts by weight of at least one polydiorganosiloxane comprising $AR^XSiO$ units terminated with endblocking $TR^XA\text{-}SiO_{1/2}$ units, wherein the polydiorganosiloxane has a viscosity of from about 100 centipoise to about 30,000,000 centipoise at 25° C. and each $R^X$ is a monovalent organic radical selected from the group consisting of hydrocarbon radicals of from 1 to 6 inclusive carbon atoms, each A radical is independently selected from $R^X$ or halohydrocarbon radicals having from 1 to 6 inclusive carbon atoms, each T radical is independently selected from the group consisting of $R^X$, OH, H or $OR^Y$, and each $R^Y$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (1), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention.

The silicon-containing capping agent according to the previous paragraphs may be selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof and may be described as to be of the general formula $XYR'_bSiZ_{3-b}$, wherein X is a monovalent radical of the general formula AE— where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0, 1 or 2. Preferably, the monovalent hydrolyzable organic radical is of the general formula R"O— where R" is an alkylene radical. Most preferably, this particular endblocking agent is selected from the group of 3-methacryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-meth-acryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl)trimethoxysilane, (methacryloxymethyl)dimethylethoxysilane, (methacryloxymethyl)methyldiethoxysilane, methacryloxymethyltriethoxysilane, methacryloxy-propyltriisopropoxysilane, 3-methacryloxypropyldimethylsilazane, 3-acryloxy-propyldimethylchlorosilane, 3-acryloxypropyldichlorosilane, 3-acryloxypropyl-trichlorosilane, 3-acryloxypropyldimethylmethoxysilane, 3-acryloxy-propylmethyldimethoxysilane, 3-acryloxypropyltrimethoxysilane, 3-acryloxypropyl-dimethylsilazane, and combinations thereof.

The ethylenically unsaturated monomer according to the previous paragraphs can be any monomer having at least one carbon-carbon double bond. Preferably, the ethylenically unsaturated monomer according to the previous paragraphs may be a compound selected from the group consisting of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms. The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl meth-acrylate, tert-butyl methacrylate, hexyl methacrylate, 2-eth-ylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

It is to be understood that the ethylenically unsaturated monomer used for preparing the silicone acrylic hybrid pressure sensitive adhesive may be more than one ethylenically unsaturated monomer. That is, a combination of ethylenically unsaturated monomers may be polymerized, more specifically co-polymerized, along with the silicon-containing pressure sensitive adhesive composition comprising acrylate or methacrylate functionality and the initiator. According to a certain embodiment of the invention, the silicone acrylic hybrid pressure-sensitive adhesive is prepared by using at least two different ethylenically unsaturated monomers, preferably selected from the group of 2-ethylhexyl acrylate and methyl acrylate, more preferably in a ratio of 50% 2-ethylhexyl acrylate and 50% methyl acrylate, or in a ratio of 60% 2-ethylhexyl acrylate and 40% methyl acrylate as the acrylic monomer.

The initiator according to the previous paragraphs may be any substance that is suitable to initiate the polymerization of the silicon-containing pressure sensitive adhesive composition comprising acrylate or methacrylate functionality and the ethylenically unsaturated monomer to form the silicone acrylic hybrid. For example, free radical initiators selected from the group of peroxides, azo compounds, redox initiators, and photo-initiators may be used.

Further suitable silicone resins, silicone polymers, silicon-containing capping agents, ethylenically unsaturated monomers, and initiators that can be used in accordance with the previous paragraphs are detailed in WO 2007/145996, EP 2 599 847 A1, and WO 2016/130408.

According to a certain embodiment of the invention, the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.

According to a certain other embodiment of the invention, the silicone acrylic hybrid polymer comprises a reaction product of a silicone polymer, a silicone resin and an acrylic polymer, wherein the silicone resin contains triorganosiloxy units $R_3SiO_{1/2}$ where R is an organic group, and tetrafunctional siloxy units $SiO_{4/2}$ in a mole ratio of from 0.1 to 0.9 $R_3SiO_{1/2}$ units for each $SiO_{4/2}$.

The acrylic polymer may comprise at least an alkoxysilyl functional monomer, polysiloxane-containing monomer, halosilyl functional monomer or alkoxy halosilyl functional monomer. Preferably, the acrylic polymer is prepared from alkoxysilyl functional monomers selected from the group consisting of trialkoxylsilyl (meth)acrylates, dialkoxyalkylsilyl (meth)acrylates, and mixtures thereof, or comprises end-capped alkoxysilyl functional groups. The alkoxysilyl functional groups may preferably be selected from the group consisting of trimethoxylsilyl groups, dimethoxymethylsilyl groups, triethoxylsilyl, diethoxymethylsilyl groups and mixtures thereof.

The acrylic polymer may also be prepared from a mixture comprising polysiloxane-containing monomers, preferably from a mixture comprising polydimethylsiloxane mono (meth)acrylate.

The silyl functional monomers will typically be used in amounts of from 0.2 to 20% by weight of the acrylic polymer, more preferably the amount of silyl functional monomers will range from about 1.5 to about 5% by weight of the acrylic polymer.

The amount of polysiloxane-containing monomer will typically be used in amounts of from 1.5 to 50% by weight of the acrylic polymer, more preferably the amount of polysiloxane-containing monomers will range from 5 to 15% by weight of the acrylic polymer.

Alternatively, the acrylic polymer comprises a block or grafted copolymer of acrylic and polysiloxane. An example of a polysiloxane block copolymer is polydimethylsiloxane-acrylic block copolymer. The preferred amount of siloxane block is 10 to 50% weight of the whole block polymer.

The acrylic polymer comprises alkyl (meth)acrylate monomers. Preferred alkyl (meth)acrylates which may be used have up to about 18 carbon atoms in the alkyl group, preferably from 1 to about 12 carbon atoms in the alkyl group. Preferred low glass transition temperature (Tg) alkyl acrylate with a homopolymer Tg of less than about 0° C. have from about 4 to about 10 carbon atoms in the alkyl group and include butyl acrylate, amyl acrylate, hexyl acrylate, 2-ethylhexyl acrylate, octyl acrylate, isooctyl acrylate, decyl acrylate, isomers thereof, and combinations thereof. Particularly preferred are butyl acrylate, 2-ethylhexyl acrylate and isooctyl acrylate. The acrylic polymer components may further comprise (meth)acrylate monomers having a high Tg such as methyl acrylate, ethyl acrylate, methyl methacrylate and isobutyl methacrylate.

The acrylic polymer component may further comprise a polyisobutylene group to improve cold flow properties of the resultant adhesive.

The acrylic polymer components may comprise nitrogen-containing polar monomers. Examples include N-vinyl pyrrolidone, N-vinyl caprolactam, N-tertiary octyl acrylamide, dimethyl acrylamide, diacetone acrylamide, N-tertiary butyl acrylamide, N-isopropyl acrylamide, cyanoethylacrylate, N-vinyl acetamide and N-vinyl formamide.

The acrylic polymer component may comprise one or more hydroxyl containing monomers such as 2-hydroxyethyl acrylate, 2-hydroxyethyl methacrylate, hydroxypropyl acrylate and/or hydroxypropyl methacrylate.

The acrylic polymer components may, if desired, comprise carboxylic acid containing monomers. Useful carboxylic acids preferably contain from about 3 to about 6 carbon atoms and include, among others, acrylic acid, methacrylic acid, itaconic acid, β-carboxyethyl acrylate and the like. Acrylic acid is particularly preferred.

Other useful, well known co-monomers include vinyl acetate, styrene, cyclohexyl acrylate, alkyl di(meth)acrylates, glycidyl methacrylate and allyl glycidyl ether, as well as macromers such as, for example, poly(styryl)methacrylate.

One acrylic polymer component that can be used in the practice of the invention is an acrylic polymer that comprises from about 90 to about 99.5% by weight of butyl acrylate and from about 0.5 to about 10% by weight dimethoxymethylsilyl methacrylate.

According to a certain embodiment of the invention the silicone acrylic hybrid polymer may be prepared by a) reacting silicone polymer with silicone resin to form a resultant product, b) reacting the resultant product of a) with an acrylic polymer containing reactive functionality, wherein the components are reacted in an organic solvent.

According to a certain embodiment of the invention the silicone acrylic hybrid polymer may be prepared by a) reacting a silicone resin with an acrylic polymer containing reactive functionality to form a resultant product, b) reacting the resultant product of a) with silicone polymer, wherein the components are reacted in an organic solvent.

According to a certain embodiment of the invention the silicone acrylic hybrid polymer may be prepared by a) reacting a silicone polymer with an acrylic polymer containing reactive functionality to form a resultant product, b) reacting the resultant product of a) with silicone resin, wherein the components are reacted in an organic solvent.

Further suitable acrylic polymers, silicone resins, and silicone polymers that can be used for chemically reacting together a silicone polymer, a silicone resin and an acrylic polymer to provide a silicone acrylic hybrid polymer in accordance with the previous paragraphs are detailed in WO 2010/124187.

According to certain embodiments of the invention, the silicone acrylic hybrid polymer used in the TTS is blended with one or more non-hybrid polymers, preferably the silicone acrylic hybrid polymer is blended with one or more non-hybrid pressure sensitive adhesives (e.g. pressure-sensitive adhesives based on polysiloxane or acrylates).

Non-Hybrid Polymers

According to a certain embodiment of the invention, the TTS comprises one or more non-hybrid polymers (e.g. non-hybrid pressure-sensitive adhesives) in addition to the silicone acrylic hybrid polymer. Non-hybrid polymers (e.g. non-hybrid pressure-sensitive adhesives) are polymers (e.g. polymer-based pressure-sensitive adhesives) which do not include a hybrid species. Preferred are non-hybrid polymers (e.g. non-hybrid pressure-sensitive adhesives) based on polysiloxanes, acrylates, polyisobutylenes, or styrene-isoprene-styrene block copolymers.

The non-hybrid polymers (e.g. the non-hybrid pressure-sensitive adhesives) may be contained in the active agent-containing layer structure and/or in the adhesive overlay.

Non-hybrid pressure-sensitive adhesives are usually supplied and used in solvents like n-heptane and ethyl acetate. The solids content of the pressure-sensitive adhesives is usually between 30% and 80%.

Suitable non-hybrid polymers according to the invention are commercially available e.g. under the brand names BIO-PSAs (pressure sensitive adhesives based on polysiloxanes), Oppanol™ (polyisobutylenes), JSR-SIS (a styrene-isoprene-styrene copolymer) or Duro-Tak™ (acrylic polymers).

Polymers based on polysiloxanes may also be referred to as silicone-based polymers. These polymers based on polysiloxanes are preferably pressure sensitive adhesives based on polysiloxanes. Pressure-sensitive adhesives based on polysiloxanes may also be referred to as silicone-based pressure-sensitive adhesives, or silicone pressure-sensitive adhesives. These pressure-sensitive adhesives based on polysiloxanes provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin (also referred to as silicate resin), a pressure-sensitive adhesive based on polysiloxane is prepared wherein for amine stability the residual silanol functionality is additionally capped with trimethylsiloxy groups. The silanol end blocked polydimethylsiloxane content contributes to the viscous component of the visco-elastic behavior, and impacts the wetting and the spreadability properties of the adhesive. The resin acts as a tackifying and reinforcing agent, and participates in the elastic component. The correct balance between silanol end blocked polydimethylsiloxane and resin provides for the correct adhesive properties.

In view of the above, silicone-based polymers, and in particular silicone-based pressure sensitive adhesives, are generally obtainable by polycondensation of silanol end-blocked polydimethylsiloxane with a silicate resin. Amine-compatible silicone-based polymers, and in particular amine-compatible silicone-based pressure sensitive adhesives, can be obtained by reacting the silicone-based polymer, in particular the silicone-based pressure sensitive adhesive, with trimethylsilyl (e.g. hexamethyldisilazane) in order to reduce the silanol content of the polymer. As a result, the residual silanol functionality is at least partly, preferably mostly or fully capped with trimethylsiloxy groups.

As indicated above, the tackiness of the silicone-based polymer may be modified by the resin-to-polymer ratio, i.e. the ratio of the silanol endblocked polydimethylsiloxane to the silicate resin, which is preferably in the range of from 70:30 to 50:50, preferably from 65:35 to 55:45. The tackiness will be increased with increasing amounts of the polydimethylsiloxane relative to the resin. High tack silicone-based polymers preferably have a resin-to-polymer ratio of 55:45, medium tack silicone-based polymers preferably have a resin-to-polymer ratio of 60:40, and low tack silicone-based polymers preferably have a resin-to-polymer ratio of 65:35. High tack silicone-based polymers preferably have a complex viscosity at 0.01 rad/s and 30° C. of about $5 \times 10^6$ Poise, medium tack silicone-based polymers preferably have a complex viscosity at 0.01 rad/s and 30° C. of about $5 \times 10^7$ Poise, and low tack silicone-based polymers preferably have a complex viscosity at 0.01 rad/s and 30° C. of about $5 \times 10^8$ Poise. High tack amine-compatible silicone-based polymers preferably have a complex viscosity at 0.01 rad/s and 30° C. of about $5 \times 10^6$ Poise, medium tack amine-compatible silicone-based polymers preferably have a complex viscosity at 0.01 rad/s and 30° C. of about $5 \times 10^8$ Poise, and low tack amine-compatible silicone-based polymers preferably have a complex viscosity at 0.01 rad/s and 30° C. of about $5 \times 10^9$ Poise.

Examples of silicone-based PSA compositions which are commercially available include the standard BIO-PSA series (7-4400, 7-4500 and 7-4600 series), the amine compatible (endcapped) BIO-PSA series (7-4100, 7-4200 and 7-4300 series) and the Soft Skin Adhesives series (7-9800) manufactured and typically supplied in n-heptane or ethyl acetate by Dow Corning. For example, BIO-PSA 7-4201 is characterized by a solution viscosity at 25° C. and about 60% solids content in heptane of 450 mPa s and a complex viscosity at 0.01 rad/s at 30° C. of $1 \times 10^8$ Poise. BIO-PSA 7-4301 has a solution viscosity at 25° C. and about 60% solids content in heptane of 500 mPa s and a complex viscosity at 0.01 rad/s at 30° C. of $5 \times 10^6$ Poise.

The pressure-sensitive adhesives based on polysiloxanes are supplied and used in solvents like n-heptane, ethyl acetate or other volatile silicone fluids. The solids content of pressure-sensitive adhesives based on polysiloxanes in solvents is usually between 60 and 85%, preferably between 70 and 80% or between 60 and 75%. The skilled person is aware that the solids content may be modified by adding a suitable amount of solvent.

Pressure-sensitive adhesives based on polysiloxanes, which are, e.g., available from Dow Corning, may be obtained according to the following scheme:

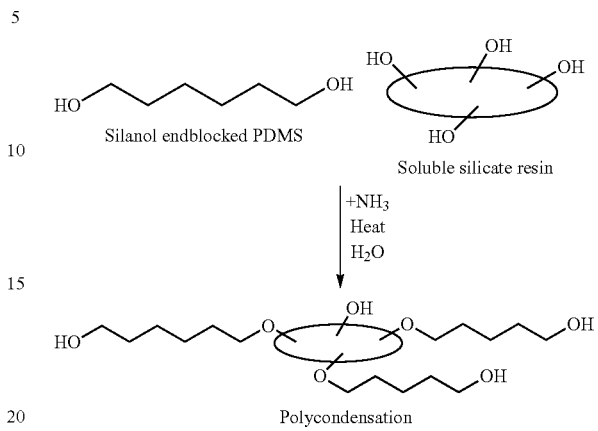

Such pressure-sensitive adhesives based on polysiloxanes are available from Dow Corning, e.g., under the tradenames BIO-PSA 7-4401, BIO-PSA-7-4501, or BIO-PSA 7-4601, which are provided in the solvent n-heptane (indicated by the code "01"), or under the tradenames BIO-PSA 7-4402, BIO-PSA 7-4502, and BIO 7-4602, which are provided in the solvent ethyl acetate (indicated by the code "02"). Typical solids contents in the solvent are in the range of from 60 to 75%. The code "44" indicates a resin-to-polymer ratio of 65:35 resulting in a low tackiness, the code "45" indicates a resin-to-polymer ratio of 60:40 resulting in medium tackiness, the code "46" indicates a resin-to-polymer ratio of 55:45 resulting in high tackiness.

Amine-compatible pressure-sensitive adhesives based on polysiloxanes, which are, e.g., available from Dow Corning may be obtained according to the following scheme:

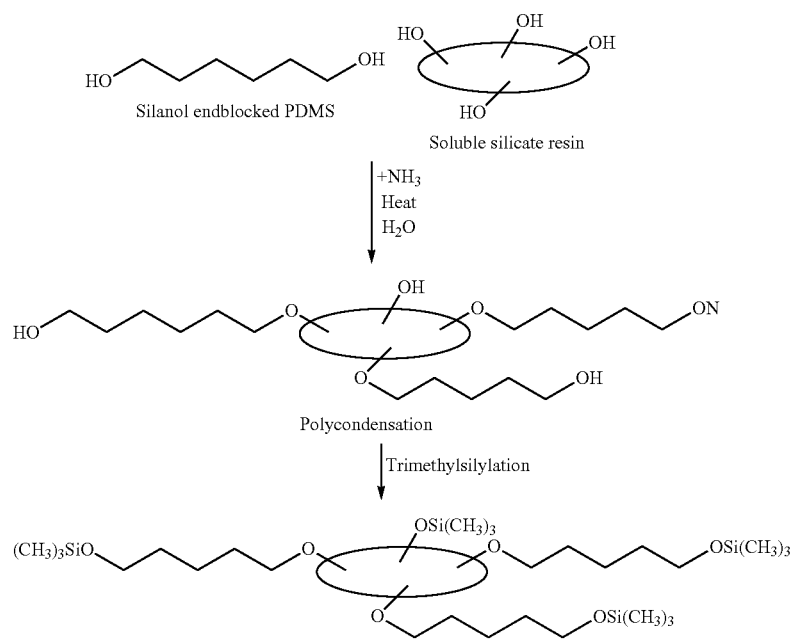

Such amine-compatible pressure-sensitive adhesives based on polysiloxanes are available from Dow Corning, e.g., under the tradenames BIO-PSA 7-4101, BIO-PSA-7-4201, or BIO-PSA 7-4301, which are provided in the solvent n-heptane (indicated by the code "01"), or under the tradenames BIO-PSA 7-4102, BIO-PSA 7-4202, and BIO 7-4302, which are provided in the solvent ethyl acetate (indicated by the code "02"). Typical solids contents in the solvent are in the range of from 60 to 75%. The code "41" indicates a resin-to-polymer ratio of 65:35 resulting in a low tackiness, the code "42" indicates a resin-to-polymer ratio of 60:40 resulting in medium tackiness, the code "43" indicates a resin-to-polymer ratio of 55:45 resulting in high tackiness.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s, preferably as measured using a Brookfield RVT viscometer equipped with a spindle number 5 at 50 rpm. Theses may also be characterized by a complex viscosity at 0.01 rad/s at 30° C. of less than about $1 \times 10^9$ Poise or from about $1 \times 10^5$ to about $9 \times 10^8$ Poise.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. A preferred example for a polyisobutylene combination is B10/B100 in a ratio of 85/15. Oppanol® B100 has a viscosity average molecular weight $M_v$ of 1,110,000, and a weight average molecular weight $M_w$ of 1,550,000, and an average molecular weight distribution $M_w/M_n$ of 2.9. Oppanol® B10 has a viscosity average molecular weight $M_v$ of 40,000, and a weight average molecular weight $M_w$ of 53,000, and an average molecular weight distribution $M_w/M_n$ of 3.2. In certain embodiments, polybutene may be added to the polyisobutylenes. The solids content of polyisobutylenes in solvents is usually between 30 and 50%, preferably between 35 and 40%. The skilled person is aware that the solids content may be modified by adding a suitable amount of solvent.

Pressure-sensitive adhesives based on acrylates may also be referred to as acrylate-based pressure-sensitive adhesives, or acrylate pressure-sensitive adhesives. Pressure-sensitive adhesives based on acrylates may have a solids content preferably between 30% and 60%. Such acrylate-based pressure-sensitive adhesives may or may not comprise functional groups such as hydroxy groups, carboxylic acid groups, neutralized carboxylic acid groups and mixtures thereof. Thus, the term "functional groups" in particular refers to hydroxy- and carboxylic acid groups, and deprotonated carboxylic acid groups.

Corresponding commercial products are available e.g. from Henkel under the tradename Duro Tak®. Such acrylate-based pressure-sensitive adhesives are based on monomers selected from one or more of acrylic acid, butylacrylate, 2-ethylhexylacrylate, glycidylmethacrylate, 2-hydroxyethylacrylate, methylacrylate, methylmethacrylate, t-octylacrylamide and vinylacetate, and are provided in ethyl acetate, heptanes, n-heptane, hexane, methanol, ethanol, isopropanol, 2,4-pentanedione, toluene or xylene or mixtures thereof.

Specific acrylate-based pressure-sensitive adhesives are available as:

Duro-Tak™ 387-2287 or Duro-Tak™ 87-2287 (a copolymer based on vinyl acetate, 2-ethylhexyl-acrylate, 2-hydroxyethyl-acrylate and glycidyl-methacrylate provided as a solution in ethyl acetate without cross-linking agent), Duro-Tak™ 387-2516 or Duro-Tak™ 87-2516 (a copolymer based on vinyl acetate, 2-ethylhexyl-acrylate, 2-hydroxyethyl-acrylate and glycidyl-methacrylate provided as a solution in ethyl acetate, ethanol, n-heptane and methanol with a titanium cross-linking agent), Duro-Tak™ 387-2051 or Duro-Tak™ 87-2051 (a copolymer based on acrylic acid, butylacrylate, 2-ethylhexylacrylate and vinyl acetate, provided as a solution in ethyl acetate and heptane), Duro-Tak™ 387-2353 or Duro-Tak™ 87-2353 (a copolymer based on acrylic acid, 2-ethylhexylacrylate, glycidylmethacrylate and methylacrylate, provided as a solution in ethyl acetate and hexane), Duro-Tak™ 87-4098 (a copolymer based on 2-ethylhexyl-acrylate and vinyl acetate, provided as a solution in ethyl acetate).

Additional polymers may also be added to enhance cohesion and/or adhesion.

Certain polymers in particular reduce the cold flow and are thus in particular suitable as additional polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prevented by the addition of certain polymers. A basic acrylate polymer (e.g. Eudragit® E100) may e.g. be used to reduce the cold flow. Thus, in certain embodiments, the matrix layer composition comprises additionally a basic polymer, in particular an amine-functional acrylate as e.g. Eudragit® E100. Eudragit® E100 is a cationic copolymer based on dimethylaminoethyl methacrylate, butyl methacrylate, and methyl methacrylate with a ratio of 2:1:1. The monomers are randomly distributed along the copolymer chain. Based on SEC method, the weight average molar mass (Mw) of Eudragit® E100 is approximately 47,000 g/mol. Further, polymers such as Plastoid B, acrylic polymers such as Eudragits, Chitosan, celluloses and derivatives thereof, and polystyrene may be useful to increase the dryness of the adhesive (e.g. the matrix layer).

Further Additives

The TTS according to the invention, and in particular the rivastigmine-containing layer may further comprise at least one additive or excipient. Said additives or excipients are preferably selected from the group consisting of crystallization inhibitors, solubilizers, fillers, substances for skincare, pH regulators, preservatives, tackifiers, softeners, stabilizers, and permeation enhancers, in particular from crystallization inhibitors, substances for skincare, tackifiers, softeners, stabilizers, and permeation enhancers. More preferably, said additives are selected from the group consisting of crystallization inhibitors, solubilizers, fillers, substances for skincare, pH regulators, preservatives, tackifiers, softeners, stabilizers, and permeation enhancers, in particular from substances for skincare, tackifiers, softeners, and stabilizers. Such additives may be present in the rivastigmine-containing layer in an amount of from 0.001% to 15% by weight, e.g. from 1 to 10% by weight or from 0.01 to 5% by weight, based on the total weight of the rivastigmine-containing layer.

It should be noted that in pharmaceutical formulations, the formulation components are categorized according to their physicochemical and physiological properties, and in accordance with their function. This means in particular that a substance or a compound falling into one category is not excluded from falling into another category of formulation component. E.g. a certain polymer can be a crystallization inhibitor but also a tackifier. Some substances may e.g. be a typical softener but at the same time act as a permeation enhancer. The skilled person is able to determine based on his general knowledge in which category or categories of formulation component a certain substance or compound belongs to. In the following, details on the excipients and additives are provided which are, however, not to be understood as being exclusive. Other substances not explicitly listed in the present description may be as well used in accordance with the present invention, and substances and/or compounds explicitly listed for one category of formulation component are not excluded from being used as another formulation component in the sense of the present invention.

In one embodiment, the rivastigmine-containing layer further comprises a crystallization inhibitor. In some embodiments, the crystallization inhibitor can be present in an amount of from 0.5 to 10% by weight based on the total weight of the rivastigmine-containing layer. Suitable examples of crystallization inhibitors include polyvinylpyrrolidone, vinyl acetate/vinylpyrrolidone copolymer and cellulose derivatives. The crystallization inhibitor is preferably polyvinylpyrrolidone, more preferably soluble polyvinylpyrrolidone. The crystallization inhibitor may increase the solubility of the active agent or inhibit the crystallization of the active agent, e.g., if the active agent is used in the form of a salt.

In one embodiment, the rivastigmine-containing layer further comprises a stabilizer, wherein the stabilizer is preferably selected from tocopherol and ester derivatives thereof and ascorbic acid and ester derivatives thereof. In some embodiments, the stabilizer can be present in an amount of from 0.001 to 2.0%, preferably from 0.01 to 1.0%, by weight based on the total weight of the rivastigmine-containing layer. In some embodiments, preferred stabilizers include sodium metabisulfite, ascorbyl esters of fatty acids such as ascorbyl palmitate, ascorbic acid, butylated hydroxytoluene, tocopherol, tocopheryl acetate and tocopheryl linoleate. Preferred stabilizers include ascorbyl esters of fatty acids, ascorbic acid, tocopherol, tocopheryl acetate and tocopheryl linoleate. Particularly preferred is tocopherol. Also particularly preferred is a combination of tocopherol and ascorbyl palmitate.

In one embodiment, the rivastigmine-containing layer further comprises a softener/plasticizer. Exemplary softeners/plasticizers include linear or branched, saturated or unsaturated alcohols having 6 to 20 carbon atoms, triglycerides and polyethylene glycols.

In one embodiment, the rivastigmine-containing layer further comprises a solubilizer. The solubilizer preferably improves the solubility of the rivastigmine in the rivastigmine-containing layer. Preferred solubilizers include, e.g., glycerol-, polyglycerol-, propylene glycol- and polyoxyethylene-esters of medium chain and/or long chain fatty acids, such as glyceryl monolinoleate, medium chain glycerides and medium chain triglycerides, non-ionic solubilisers made by reacting castor oil with ethylene oxide, and any mixtures thereof which may further contain fatty acids or fatty alcohols; cellulose and methylcellulose and derivatives thereof such as hydroxypropylcellulose and hypromellose acetate succinate; various cyclodextrins and derivatives thereof; non-ionic tri-block copolymers having a central hydrophobic chain of polyoxypropylene flanked by two hydrophilic chains of polyoxyethylene known as poloxamers; water-soluble derivatives of vitamin E; pharmaceutical graded or agglomerated spherical isomalt; a polyethylene glycol, polyvinyl acetate and polyvinylcaprolactame-based graft copolymer, also abbreviated as PVAc-PVCap-PEG and known as Soluplus®; purified grades of naturally derived castor oil, of polyethylene glycol 400, of polyoxyethylene sorbitan monooleate (such as polysorbate 80) or of propylene glycols; diethylene glycol monoethyl ether; gluconodelta-lactone; maize and potato starch; as well as any of the below mentioned soluble polyvinylpyrrolidones, but also insoluble/cross-linked polyvinylpyrrolidones such as crospovidones.

However, also the permeation enhancers mentioned below can act as solubilizers. Furthermore, also crystallization inhibitors may act as solubilizers.

In one embodiment, the rivastigmine-containing layer further comprises a pH regulator. Suitable pH regulators include mild acids and bases including amine derivatives, inorganic alkali derivatives, and polymers with basic or acidic functionality.

In one embodiment, the rivastigmine-containing layer further comprises a preservative. Suitable preservatives include parabens, formaldehyde releasers, isothiazolinones, phenoxyethanol, and organic acids such as benzoic acid, sorbic acid, levulinic acid and anisic acid.

In one embodiment, the rivastigmine-containing layer further comprises a substance for skincare. Such substances may be used to avoid or reduce skin irritation as detectable by the dermal response score. Suitable substances for skincare include sterol compounds such as cholesterol, dexpanthenol, alpha-bisabolol, and antihistamines. Substances for skincare are preferably used in amounts of from 1 to 10% by weight based on the total weight of the rivastigmine-containing layer.

If the rivastigmine-containing layer is required to have self-adhesive properties and one or more polymers is/are selected, which does/do not provide sufficient self-adhesive properties, a tackifier is added. Preferred tackifiers include Miglyol, which is a liquid wax ester based on long-chain, unsaturated, even-numbered fatty acids and long-chain, unsaturated, even-numbered fatty alcohols of vegetable origin, and polyethyleneglycols. In particular, the tackifier may be selected from polyvinylpyrrolidone (which, due to its ability to absorb water, is able to maintain the adhesive properties of the matrix layer and thus can be regarded as a tackifier in a broad sense), triglycerides, polyethylene glycols, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone. Preferably, the tackifier may be selected from polyvinylpyrrolidone, triglycerides, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone. In some embodiments, the tackifier can be present in an amount of from 5 to 15% by weight based on the total weight of the rivastigmine-containing layer.

The term "soluble polyvinylpyrrolidone" refers to polyvinylpyrrolidone, also known as povidone, which is soluble with more than 10% in at least ethanol, preferably also in water, diethylene glycol, methanol, n-propanol, 2 propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F. The different grades of Kollidon® are defined in terms of the K-Value reflecting the average molecular weight of the polyvinylpyrrolidone grades. Kollidon® 12 PF is characterized by a K-Value range of 10.2 to 13.8, corresponding to a nominal K-Value of 12. Kollidon® 17 PF is characterized by a K-Value range of 15.3 to 18.4, corresponding to a nominal K-Value of 17. Kollidon® 25 is characterized by a K-Value range of 22.5 to 27.0, corresponding to a nominal K-Value of 25, Kollidon® 30 is characterized by a K-Value range of 27.0 to 32.4, corresponding to a nominal K-Value of 30. Kollidon® 90 F is characterized by a K-Value range of 81.0 to 97.2, corresponding to a nominal K-Value of 90. Preferred Kollidon® grades are Kollidon® 12 PF, Kollidon® 30 and Kollidon® 90 F.

Within the meaning of this invention, the term "K-Value" refers to a value calculated from the relative viscosity of polyvinylpyrrolidone in water according to the European Pharmacopoeia (Ph.Eur.) and USP monographs for "Povidone".

Fillers such as silica gels, titanium dioxide and zinc oxide may be used in conjunction with the polymer in order to influence certain physical parameters, such as cohesion and bond strength, in the desired way.

In one embodiment, the rivastigmine-containing layer further comprises a permeation enhancer. Permeation enhancers are substances, which influence the barrier properties of the stratum corneum in the sense of increasing the active agent permeability. Some examples of permeation enhancers are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methylcetylsulfoxide, dimethylaurylamine, dodecyl pyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate.

If the rivastigmine-containing layer further comprises a permeation enhancer, the permeation enhancer is preferably selected from diethylene glycol monoethyl ether (transcutol), diisopropyl adipate, isopropyl myristate, isopropyl palmitate, lauryl lactate, and dimethylpropylene urea.

It has been found that the TTS provides sufficient permeability of the active agent even if no permeation enhancer is present. Therefore, in certain embodiments of the invention, the rivastigmine-containing layer does not comprise a permeation enhancer or solubilizer.

Release Characteristics

The TTS in accordance with the invention are designed for transdermally administering rivastigmine to the systemic circulation for a predefined extended period of time, preferably for 24 hours.

In one embodiment, the TTS according to the invention provides by transdermal delivery a mean release rate of from 150 to 3500 $\mu g/cm^2$*day, preferably from 200 to 3000 $\mu g/cm^2$*day rivastigmine over about 24 hours of administration.

In one embodiment, the TTS according to the invention provides by transdermal delivery from 2 to 20 mg of rivastigmine at an approximately constant rate, during an administration period of the TTS to the skin of the patient for about 24 hours.

In one embodiment, the TTS according to the invention provides by transdermal delivery at steady state a plasma concentration of rivastigmine of from 1 to 25 ng/ml, preferably from 1 to 20 ng/ml.

Preferably, the TTS provides therapeutically effective plasma concentrations of rivastigmine within less than 8 hours, preferably less than 6 hours, more preferably less than 4 hours after application of the TTS to the skin.

Preferably, the TTS provides, after a steady state of the plasma concentration is reached, a therapeutically effective steady state plasma concentration of rivastigmine for at least 12 hours, preferably at least 18 hours, more preferably at least 20 hours, provided that the TTS is administered to the skin for a sufficient time, e.g., for at least 24 hours, so that the steady state can be reached and maintained. In particular, the TTS ensures that a plasma concentration of rivastigmine of from 1 ng/ml to 25 ng/ml is reached within less than 8 hours, preferably less than 6 hours, more preferably less than 4 hours, and that this plasma concentrations is maintained for at least 12 hours, preferably at least 18 hours, more preferably at least 20 hours, if the TTS is administered to the skin of the patient for about 24 hours.

In one embodiment, the TTS according to the invention provides an $AUC_{24h}$ of about 10 to 450 ng*h/ml, preferably of about 20 to 340 ng*h/ml, after repeated once daily administration. In another embodiment, the TTS according to the invention provides, a $C_{max}$ of about 0.5 to 30 ng/ml, preferably of about 1 to 25 ng/ml, after applying the transdermal therapeutic system on the skin of the patient. In yet another embodiment, the TTS according to the invention provides a $t_{max}$ of about 3 to 15 hours, preferably of about 5 to 10 hours, after applying the transdermal therapeutic system on the skin of the patient.

In one embodiment, the TTS according to the invention provides a plasma concentration of rivastigmine as analyzed using LC-MS/MS with a lower limit of quantification (LLOQ) of 0.1 ng/ml of
0 ng/ml to 15 ng/ml in the first 4 hours,
1 ng/ml to 22 ng/ml from hour 4 to hour 12,
0.5 ng/ml to 14 ng/ml from hour 12 to hour 24.

In one embodiment, the transdermal therapeutic system according to the invention provides a cumulative permeated amount of rivastigmine as measured in a Franz diffusion cell with an EVA membrane of about 300 $\mu g/cm^2$ to 1200 $\mu g/cm^2$ over a time period of 24 hours.

In one embodiment, the transdermal therapeutic system according to the invention provides a permeated amount of rivastigmine as measured in a Franz diffusion cell with EVA-membrane (9% vinyl acetate Cotran 9702 von 3M) of
0 $\mu g/cm^2$ to 240 $\mu g/cm^2$ in the first 3 hours,
80 $\mu g/cm^2$ to 350 $\mu g/cm^2$ from hour 3 to hour 8,
210 $\mu g/cm^2$ to 560 mg/cm$^2$ from hour 8 to hour 24.

Method of Treatment/Medical Use

In accordance with a specific aspect of the present invention, the TTS according to the invention is for use in a method of treating a human patient, preferably for use in a method of preventing, treating, or delaying of progression of Alzheimer's disease, dementia associated with Parkinson's disease, and/or symptoms of traumatic brain injury. According to another specific aspect of the present invention, the TTS is for use in a method of treating a human patient, preferably for use in a method of treating mild to moderate dementia caused by Alzheimer's or Parkinson's disease.

In one embodiment, the TTS according to the invention is for use in a method of treating a human patient, preferably for use in a method of treating a human patient, preferably for use in a method of preventing, treating, or delaying of progression of Alzheimer's disease, dementia associated with Parkinson's disease, and/or symptoms of traumatic brain injury, or for use in a method of treating a human patient, preferably for use in a method of treating mild to moderate dementia caused by Alzheimer's or Parkinson's disease, wherein the transdermal therapeutic system is applied to the skin of the patient for a dosing interval of at least 24 hours, preferably about 24 hours.

In one embodiment, the TTS according to the invention is for use in a method of treating a human patient, preferably for use in a method of treating a human patient, preferably for use in a method of preventing, treating, or delaying of progression of Alzheimer's disease, dementia associated with Parkinson's disease, and/or symptoms of traumatic brain injury, or for use in a method of treating a human patient, preferably for use in a method of treating mild to moderate dementia caused by Alzheimer's or Parkinson's disease, wherein the transdermal therapeutic system is applied to the skin of the patient for a dosing interval of at least 72 hours, preferably about 84 hours.

In certain embodiments, the present invention relates to a method of treating a human patient, in particular preventing, treating, or delaying of progression of Alzheimer's disease, dementia associated with Parkinson's disease, and/or symptoms of traumatic brain injury, by applying a transdermal therapeutic system as defined within the invention to the skin of the patient. In another certain embodiment, the present invention relates to a method of treating a human patient, in particular treating a mild to moderate dementia caused by Alzheimer's and Parkinson's disease, by applying a transdermal therapeutic system as defined within the invention to the skin of the patient.

In one embodiment, the present invention relates to a method of treating a human patient, in particular preventing, treating, or delaying of progression of Alzheimer's disease, dementia associated with Parkinson's disease, and/or symptoms of traumatic brain injury, or a method of treating a human patient, in particular treating a mild to moderate dementia caused by Alzheimer's and Parkinson's disease, wherein the transdermal therapeutic system is applied to the skin of the patient for a dosing interval of at least 24 hours, preferably about 24 hours.

In one embodiment, the present invention relates to a method of treating a human patient, in particular preventing, treating, or delaying of progression of Alzheimer's disease, dementia associated with Parkinson's disease, and/or symptoms of traumatic brain injury, or a method of treating a human patient, in particular treating a mild to moderate dementia caused by Alzheimer's and Parkinson's disease, wherein the transdermal therapeutic system is applied to the skin of the patient for a dosing interval of at least 72 hours, preferably about 84 hours.

In connection with the above uses and methods of treatment, the TTS according to the invention is preferably applied to at least one body surface on the subject selected from the upper outer art, upper chest, upper back or the side of the chest for the defined dosing intervals.

The preferred application time of a TTS according to the invention is at least 24 hours, preferably about 24 hours (1 day) or about 84 hours (3.5 days), particularly preferably about 24 hours. After this time, the TTS may be removed, and optionally a new TTS may be applied, so as to allow an around-the-clock treatment.

Process of Manufacture

The invention further relates to a process of manufacture of a rivastigmine-containing layer, preferably a rivastigmine-containing matrix layer, for use in a transdermal therapeutic system.

In accordance with the invention, the process for manufacturing a rivastigmine-containing layer for use in a transdermal therapeutic system according to the invention comprises the steps of:
1) combining at least the components
   1. rivastigmine in an amount such that the amount of rivastigmine in the resulting rivastigmine-containing layer is from 10 to 25% by weight based on the total weight of the rivastigmine-containing layer;
   2. a silicone acrylic hybrid polymer; and
   3. optionally at least one additional non-hybrid polymer and/or additive; to obtain a coating composition;
2) coating the coating composition onto the backing layer or release liner; and
3) drying the coated coating composition to form the rivastigmine-containing layer.

In step 1) of the above process of manufacture, the rivastigmine is preferably dissolved or dispersed to obtain a homogenous coating composition.

In the above described process, the solvent is preferably selected from alcoholic solvents, in particular methanol, ethanol, isopropanol and mixtures thereof, and from non-alcoholic solvents, in particular ethyl acetate, hexane, heptane, petroleum ether, toluene, and mixtures thereof, and is more preferably selected from non-alcoholic solvents, and is most preferably ethyl acetate or n-heptane.

In certain embodiments of the present invention, the silicone acrylic hybrid polymer is provided as a solution, wherein the solvent is ethyl acetate or n-heptane. Preferably ethyl acetate is used. Preferably, the silicone acrylic hybrid polymer has a solids content of from 40 to 60% by weight.

In step 3) of the above process of manufacture, drying is performed preferably at a temperature of from 20 to 90° C., more preferably from 40 to 70° C.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Comparative Example 1

Comparative Example 1 (Comp. 1) is the commercially available rivastigmine-containing TTS product Exelon®, having a rivastigmine-containing acrylic based layer (60 g/m²) and a rivastigmine-free silicone based skin contact layer (30 g/m²), provided by Novartis Pharma.

The permeated amount of the commercially available Exelon® TTS was determined in accordance to Examples 1 to 7 and the corresponding cumulated amount at 24 hours was calculated.

The results are shown in Tables 2.2, 4.2, 5.2, and 6.2 and in FIGS. 1 to 7.

Example 1a-d

Coating Composition

The formulation of the rivastigmine-containing coating composition of Examples 1a-d are summarized in Table 1.1a and 1.1b below. The %-values refer to the amounts in % by weight.

TABLE 1.1

| Ingredient (Trade Name) | Ex. 1a Amt [g] | Ex. 1a Solids [%] | Ex. 1b Amt [g] | Ex. 1b Solids [%] |
|---|---|---|---|---|
| Rivastigmine base | 4.01 | 20.02 | 4.22 | 20.86 |
| Silicone acrylic hybrid pressure sensitive adhesive in ethyl acetate Solids content of 50.1% by weight (PSA SilAc 7-6102 from Dow Corning Healthcare) | 31.98 | 79.98 | 23.97 | 59.35 |
| Silicone adhesive in n-heptane Solids content of 61.9% by weight (DOW CORNING ® BIO-PSA Q7-4202) | — | — | 6.47 | 19.79 |
| Total | 35.99 | 100.0 | 34.66 | 100.0 |
| Area Weight [g/m²] | 98.0 | | 92.4 | |
| Loading API [µg/cm²] | 1962 | | 1927 | |

| Ingredient (Trade Name) | Ex. 1c Amt [g] | Ex. 1c Solids [%] | Ex. 1d Amt [g] | Ex. 1d Solids [%] |
|---|---|---|---|---|
| Rivastigmine base | 4.02 | 20.07 | 4.00 | 19.98 |
| Silicone acrylic hybrid pressure sensitive adhesive in n-heptane Solids content of 50.4% by weight (PSA SilAc 7-6301 from Dow Corning Healthcare) | 31.76 | 79.93 | 23.81 | 59.95 |
| Acrylate adhesive in ethyl acetate Solids content of 38.4% by weight (DURO-TAK ® 387-4098) | — | — | 10.46 | 20.07 |
| Total | 35.78 | 100.0 | 38.27 | 100.0 |
| Area Weight [g/m²] | 91.8 | | 84.7 | |
| Loading API [µg/cm²] | 1842 | | 1692 | |

Preparation of the Coating Composition

A beaker was loaded with the silicone acrylic hybrid pressure-sensitive adhesive having a solids content of about 50% by weight (PSA SilAc 7-6102 from Dow Corning Healthcare for Ex. 1a and 1b or PSA SilAc 7-6301 from Dow Corning Healthcare for Ex. 1c and 1d). The rivastigmine base and, if applicable (Ex. 1b and 1d), the additional adhesive was added under stirring. The mixture was stirred at about 800 rpm until a homogenous mixture was obtained (at least 20 min).

Coating of the Coating Composition

The resulting rivastigmine-containing coating composition was coated within less than 24 h after the rivastigmine-containing mixture was finished on an adhesively equipped foil (Scotchpak 9755 AB1F) using hand over knife lab coating equipment, using an erichson coater. The solvent was removed by drying in a first step at about room temperature (23±2° C.) for about 10 min, followed by a second drying step at about 60° C. (about 70° C. for Ex. 1a) for about 20 min (about 10 min for Ex. 1a).

The coating thickness was chosen such that removal of the solution results in an area weight of the rivastigmine-containing layer of about 98.0 (Ex. 1a), 92.4 (Ex. 1b), 91.8 (Ex. 1c), and 84.7 (Ex. 1d) g/m². The dried film was then laminated with a backing layer (FO PET 23 µm transparent).

Preparation of the TTS (Concerning all Examples)

The individual systems (TTS) were punched out from the rivastigmine-containing self-adhesive layer structure obtained as described above. Then, the TTS were sealed into pouches of the primary packaging material.

Measurement of Permeated Amount

The permeated amount of TTS prepared according to Examples 1a-d was determined by experiments in accordance with the EMA Guideline on quality of transdermal patches (adopted Oct. 23, 2014) carried out with a 10.0 ml Franz diffusion cell, wherein EVA-membrane (9% vinyl acetate; Scotchpak Cotran 9702 from 3M) having a thickness of 50 µm was used. Diecuts with an area of release of 1.156 cm² were punched from the TTS. The TTS was applied to the EVA-membrane by using an adhesive overly. The rivastigmine permeated amount in the receptor medium of the Franz diffusion cell (phosphate buffer solution pH 5.5 with 0.1% sodium azide as antibacteriological agent) at a temperature of 32±1° C. was measured and the corresponding cumulated amount at 24 hours was calculated.

The results are shown in Table 1.2 and FIG. 1.

TABLE 1.2

| | permeated amount with SD [µg/cm²] | | | | | | | |
|---|---|---|---|---|---|---|---|---|
| Elapsed time [h] | Ex. 1a (n = 3) | | Ex. 1b (n = 3) | | Ex. 1c (n = 3) | | Ex. 1d (n = 3) | |
| | Amount | SD | Amount | SD | Amount | SD | Amount | SD |
| 3 | 100.91 | 1.96 | 118.85 | 2.35 | 120.82 | 1.72 | 98.06 | 3.61 |
| 6 | 101.18 | 1.67 | 122.72 | 6.31 | 129.56 | 3.92 | 104.45 | 3.24 |
| 8 | 65.93 | 4.36 | 80.6 | 3.72 | 85.53 | 2.81 | 67.88 | 4.83 |
| 24 | 430.58 | 20.61 | 482.19 | 26.37 | 509.03 | 26.13 | 438.11 | 4.33 |
| Cum. at 24 h | 698.6 | 23.8 | 804.36 | 36.4 | 844.94 | 31.4 | 708.5 | 15.2 |

Coating Composition

The formulation of the rivastigmine-containing coating composition of Examples 2a-c are summarized in Table 2.1 below. The %-values refer to the amounts in % by weight.

TABLE 2.1

| Ingredient (Trade Name) | Ex. 2a Amt [g] | Ex. 2a Solids [%] | Ex. 2b Amt [g] | Ex. 2b Solids [%] | Ex. 2c Amt [g] | Ex. 2c Solids [%] |
|---|---|---|---|---|---|---|
| Rivastigmine base | 4.00 | 20.02 | 5.00 | 23.81 | 4.00 | 19.96 |
| Silicone acrylic hybrid pressure sensitive adhesive in ethyl acetate Solids content of 50.9% by weight (PSA SilAc 7-6302 from Dow Corning Healthcare) | 19.64 | 50.04 | 19.65 | 47.63 | 23.57 | 59.88 |
| Acrylate adhesive in ethyl acetate Solids content of 38.4% by weight (DURO-TAK ® 387-4098) | 15.58 | 29.94 | 15.62 | 28.56 | — | — |
| Acrylate polymer in ethyl acetate Solids content of 40.6% by weight (Eudragit E100) | — | — | — | — | 9.95 | 20.16 |
| Total | 39.22 | 100.0 | 40.27 | 100.0 | 37.52 | 100.0 |
| Area Weight [g/m$^2$] | | 82.3 | | 110.3 | | 98.9 |
| Loading API [µg/cm$^2$] | | 1648 | | 2626 | | 1974 |

Preparation of the Coating Composition

The coating composition was prepared as described in Example 1, wherein the respective silicone acrylic hybrid pressure sensitive adhesive (PSA SilAc 7-6302 from Dow Corning Healthcare) and the respective additional adhesive DURO-TAKO 387-4098 for Ex. 2a and 2b and polymer Eudragit E100 for Ex. 2c, was used.

Coating of the Coating Composition

See Example 1b-d for the coating process. The coating thickness gave an area weight of the rivastigmine-containing layer of 82.3 (Ex. 2a), 110.3 (Ex. 2b), and 98.9 (Ex. 2c) g/m$^2$. The dried film was laminated with a polyethylene terephthalate backing layer (FO PET 23 µm transparent) to provide a rivastigmine-containing self-adhesive layer structure.

Preparation of the TTS

See Example 1.

Measurement of Permeated Amount

The permeated amount of TTS prepared according to Examples 2a-c as well as the commercially available Exelon® was determined as described for Examples 1a-d above.

Figure 2:
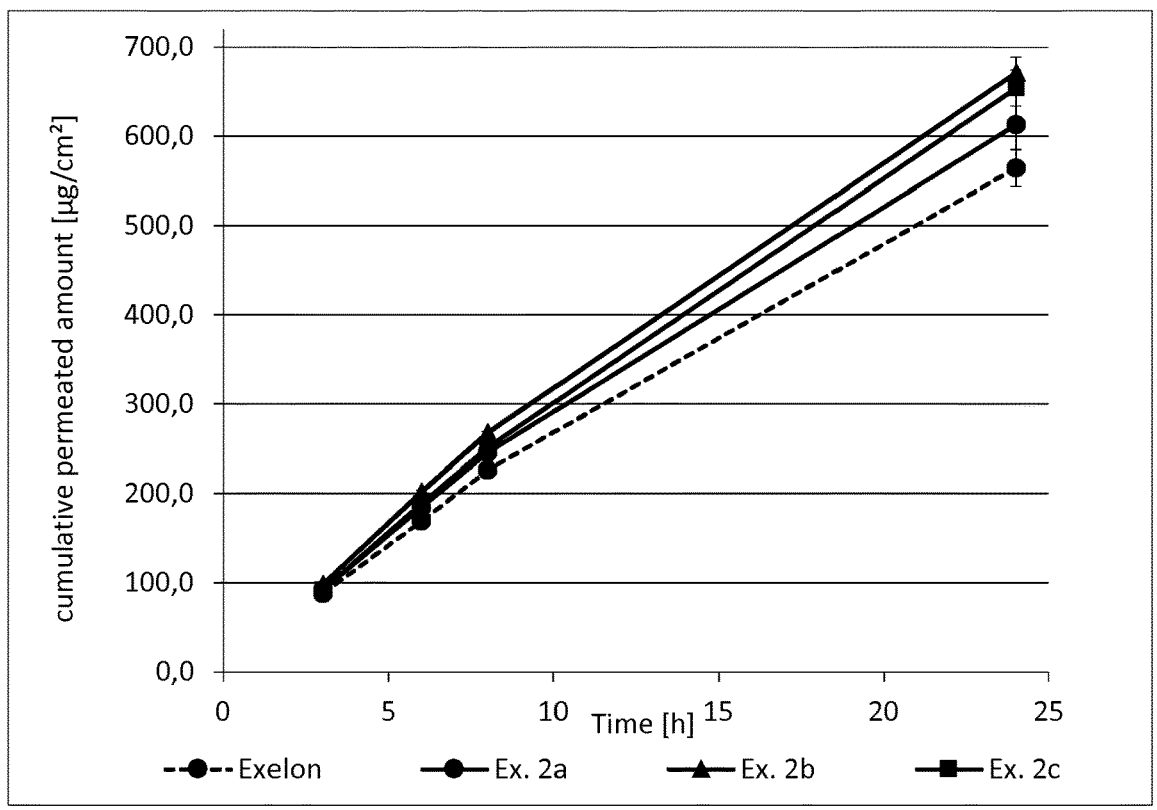
FIG. 2 depicts the rivastigmine cumulative permeated amount of TTS prepared according to Examples 2a-c and Exelon.

The results are shown in Tables 2.2 and FIG. 2.

TABLE 2.2

| | Permeated amount with SD [µg/cm$^2$] | | | | | | | |
|---|---|---|---|---|---|---|---|---|
| Elapsed time [h] | Ex. 2a (n = 3) | | Ex. 2b (n = 3) | | Ex. 2c (n = 3) | | Exelon ® (n = 3) | |
| | Amount | SD | Amount | SD | Amount | SD | Amount | SD |
| 3 | 91.5 | 3.56 | 98.11 | 2.19 | 91.74 | 2.3 | 87.97 | 2.44 |
| 6 | 92.83 | 6 | 103.43 | 0.25 | 96.98 | 4.67 | 80.67 | 4.05 |
| 8 | 61.2 | 4 | 65.75 | 0.73 | 62.34 | 3.94 | 57.2 | 4.11 |
| 24 | 367.38 | 32.9 | 403.58 | 18.53 | 402.79 | 14.23 | 338.51 | 15.64 |
| Cum. at 24 h | 612.91 | 48.5 | 670.87 | 18.1 | 653.85 | 20.1 | 564.35 | 20.5 |

Example 3a, 3b

The formulation of the rivastigmine-containing coating composition of Examples 3a and 3b are summarized in Table 3.1 below. The %-values refer to the amounts in % by weight.

TABLE 3.1

| Ingredient (Trade Name) | Ex. 3a Amt [g] | Ex. 3a Solids [%] | Ex. 3b Amt [g] | Ex. 3b Solids [%] |
|---|---|---|---|---|
| Rivastigmine base | 3.03 | 15.13 | 3.00 | 15.00 |
| Silicone acrylic hybrid pressure sensitive adhesive in ethyl acetate Solids content of 50.1% by weight (PSA SilAc 7-6102 from Dow Corning Healthcare) | 33.92 | 84.87 | — | — |
| Silicone acrylic hybrid pressure sensitive adhesive in ethyl acetate Solids content of 50.9% by weight (PSA SilAc 7-6302 from Dow Corning Healthcare) | — | — | 33.39 | 85.00 |
| Total | 36.95 | 100.0 | 36.39 | 100.0 |
| Area Weight [g/m$^2$] | | 92.1 | | 93.3 |
| Loading API [µg/cm$^2$] | | 1393 | | 1400 |

Preparation of the Coating Composition

The coating composition was prepared as described in Example 1, wherein the respective silicone acrylic hybrid pressure sensitive adhesive PSA SilAc 7-6102 from Dow Corning Healthcare (Ex. 3a) or PSA SilAc 7-6302 from Dow Corning Healthcare (Ex. 3b), was used.

Coating of the Coating Composition

See Example 1a for the coating process. The coating thickness gave an area weight of the rivastigmine-containing layer of 92.1 (Ex. 3a) and 93.3 (Ex. 2b) g/m². The dried film was laminated with a polyethylene terephthalate backing layer (FO PET 23 µm transparent) to provide a rivastigmine-containing self-adhesive layer structure.

Preparation of the TTS

See Example 1.

Measurement of Permeated Amount

The permeated amount of TTS prepared according to Examples 3a and 3b was determined as described for Examples 1a-d above.

Figure 3:
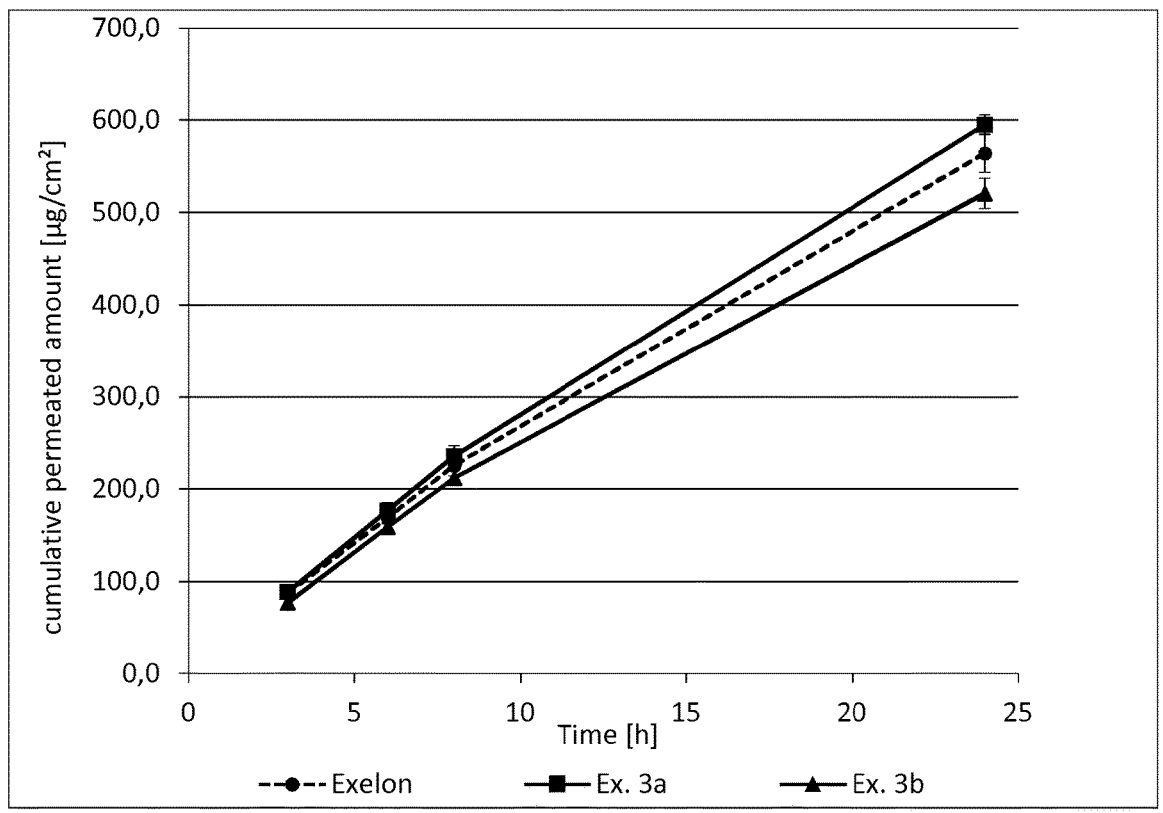
FIG. 3 depicts the rivastigmine cumulative permeated amount of TTS prepared according to Examples 3a and 3b, and Exelon.

The results are shown in Table 3.2 and FIG. 3.

TABLE 3.2

| Elapsed time [h] | Permeated amount with SD [µg/cm²] | | | |
|---|---|---|---|---|
| | 3a (n = 3) | | 3b (n = 3) | |
| | Amount | SD | Amount | SD |
| 3 | 88.82 | 5.57 | 77.12 | 4.6 |
| 6 | 87.74 | 3.63 | 81.89 | 1.08 |
| 8 | 59.19 | 2.79 | 53.31 | 2.66 |
| 24 | 359.27 | 1.12 | 308.35 | 17.35 |
| Cum. at 24 h | 595.02 | 11.0 | 520.67 | 16.4 |

Example 4a-d

Coating Composition

The formulation of the rivastigmine-containing coating composition of Examples 4a-d are summarized in Table 4.1a and 4.1b below. The %-values refer to the amounts in % by weight.

TABLE 4.1

| Ingredient (Trade Name) | Ex. 4a | | Ex. 4b | |
|---|---|---|---|---|
| | Amt [g] | Solids [%] | Amt [g] | Solids [%] |
| Rivastigmine base | 4.03 | 20.11 | 4.08 | 20.29 |
| Silicone acrylic hybrid pressure sensitive adhesive in n-heptane; Solids content of 49.7% by weight (PSA SilAc 7-6101 from Dow Corning Healthcare) | 32.20 | 79.89 | 24.19 | 59.79 |
| Silicone adhesive in n-heptane Solids content of 72.8% by weight (DOW CORNING ® BIO-PSA Q7-4201) | — | — | 5.50 | 19.91 |
| Total | 36.23 | 100.0 | 33.77 | 100.0 |
| Area Weight [g/m²] | 70.8 | | 76.8 | |
| Loading API [µg/cm²] | 1424 | | 1558 | |

TABLE 4.1-continued

| Ingredient (Trade Name) | Ex. 4c (0084) | | Ex. 4d (0085) | |
|---|---|---|---|---|
| | Amt [g] | Solids [%] | Amt [g] | Solids [%] |
| Rivastigmine base | 4.00 | 20.00 | 3.99 | 19.91 |
| Silicone acrylic hybrid pressure sensitive adhesive in ethyl acetate Solids content of 50.9% by weight (PSA SilAc 7-6302 from Dow Corning Healthcare) | 23.57 | 60.00 | 23.58 | 59.90 |
| Acrylate adhesive in ethyl acetate Solids content of 36% by weight (DURO-TAK ® 387-2353) | 11.11 | 20.00 | — | — |
| Acrylate adhesive in ethyl acetate Solids content of 38.6% by weight (DURO-TAK ® 387-4098) | — | — | 10.48 | 20.19 |
| Ethyl acetate | 10.22 | — | — | — |
| Total | 48.9 | 100.0 | 38.05 | 100.0 |
| Area Weight [g/m²] | 77.5 | | 84.2 | |
| Loading API [µg/cm²] | 1550 | | 1676 | |

Preparation of the Coating Composition

A beaker was loaded with the silicone acrylic hybrid pressure-sensitive adhesive having a solids content of about 50% by weight (PSA SilAc 7-6101 from Dow Corning Healthcare for Ex. 4a and 4b or PSA SilAc 7-6302 from Dow Corning Healthcare Ex. 4c and 4d). The rivastigmine base and, if applicable (Ex. 4b, 4c, and 4d), the additional adhesive was added under stirring. If applicable, the solvent (ethyl acetate for Ex. 4c) was added. The mixture was stirred at about 800 rpm until a homogenous mixture was obtained (at least 20 min).

Coating of the Coating Composition

The resulting rivastigmine-containing coating composition was coated within less than 24 h after the rivastigmine-containing mixture was finished on an adhesively equipped foil (Scotchpak 9755 AB1F) using hand over knife lab coating equipment, using an erichson coater. The solvent was removed by drying in a first step at about room temperature (23±2° C.) for about 10 min, followed by a second drying step at about 70° C. for about 10 min.

The coating thickness was chosen such that removal of the solution results in an area weight of the rivastigmine-containing layer of about 70.8 (Ex. 4a), 76.8 (Ex. 4b), 77.5 (Ex. 4c), and 84.2 (Ex. 4d) g/m². The dried film was then laminated with a backing layer (FO PET 23 µm transparent).

Preparation of the TTS (Concerning all Examples)

See Example 1.

Measurement of Permeated Amount

The permeated amount of TTS prepared according to Examples 4a-d and of the commercially available Exelon® TTS was determined by experiments in accordance with the EMA Guideline on quality of transdermal patches (adopted Oct. 23, 2014) carried out with a 10.0 ml Franz diffusion cell, wherein EVA-membrane (9% vinyl acetate; Scotchpak Cotran 9702 from 3M) having a thickness of 50 µm was used. Diecuts with an area of release of 1.156 cm² were punched from the TTS. The rivastigmine permeated amount in the receptor medium of the Franz diffusion cell (phosphate buffer solution pH 5.5 with 0.1% sodium azide as antibacteriological agent) at a temperature of 32±1° C. was measured and the corresponding cumulated amount at 24 hours was calculated.

Figure 4:
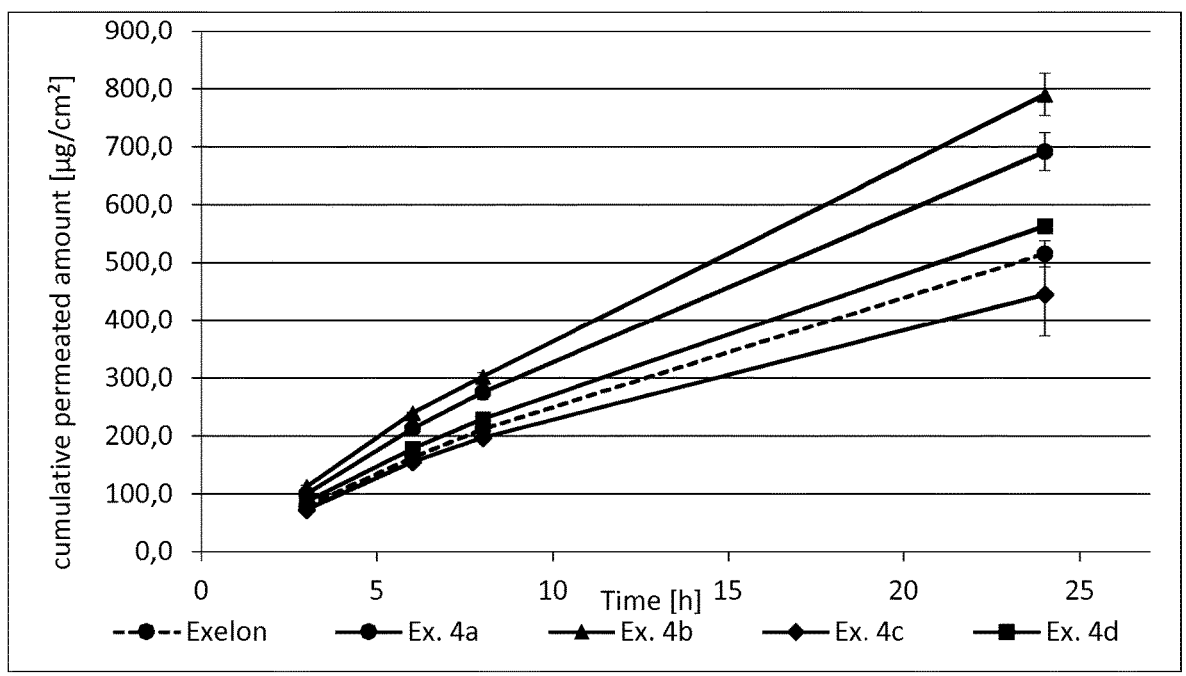
FIG. 4 depicts the rivastigmine cumulative permeated amount of TTS prepared according to Examples 4a-d and Exelon.

The results are shown in Tables 4.2 and FIG. 4.

TABLE 4.2

| | \multicolumn{10}{c}{Permeated amount with SD [µg/cm$^2$]} |
|---|---|---|---|---|---|---|---|---|---|---|
| Elapsed time [h] | Ex. 4a (n = 3) | | Ex. 4b (n = 3) | | Ex. 4c (n = 3) | | Ex. 4d (n = 3) | | Exelon ® (n = 3) | |
| | Amt | SD | Amt | SD | Amt | SD | Amot | SD | Amt | SD |
| 3 | 100.07 | 1.22 | 112.04 | 2.67 | 73 | 0.96 | 86.37 | 3.26 | 79.12 | 2.25 |
| 6 | 112.76 | 2.4 | 128.22 | 1.66 | 82.51 | 6.5 | 91.85 | 5.12 | 83.54 | 1.64 |
| 8 | 61.94 | 11.02 | 61.72 | 6.65 | 41.79 | 0.7 | 51.51 | 4.43 | 48.4 | 2.05 |
| 24 | 416.55 | 25.15 | 488.2 | 39.78 | 247.65 | 65.29 | 333.26 | 6.16 | 304.26 | 19.61 |
| Cum. at 24 h | 691.32 | 32.8 | 790.18 | 36.6 | 444.95 | 72.2 | 562.99 | 4.4 | 515.32 | 22.8 |

Example 5a-d

Coating Composition

The formulation of the rivastigmine-containing coating composition of Examples 5a-d are summarized in Table 5.1a and 5.1b below. The %-values refer to the amounts in % by weight.

TABLE 5.1

| Ingredient (Trade Name) | Ex. 5a | | Ex. 5b | |
|---|---|---|---|---|
| | Amt [g] | Solids [%] | Amt [g] | Solids [%] |
| Rivastigmine base | 4.00 | 19.84 | 3.50 | 17.50 |
| Silicone acrylic hybrid pressure sensitive adhesive in ethyl acetate Solids content of 50.9% (Ex. 5a) or 50.3% (Ex. 5b) by weight (PSA SilAc 7-6302 from Dow Corning Healthcare) | 27.53 | 69.50 | 32.80 | 82.50 |
| Acrylate adhesive in ethyl acetate Solids content of 38.4% by weight (DURO-TAK ® 387-4098) | 5.60 | 10.66 | — | — |
| Total | 37.13 | 100.0 | 36.30 | 100.0 |
| Area Weight [g/m$^2$] | 93.1 | | 107.7 | |
| Loading API [µg/cm$^2$] | 1847 | | 1885 | |

| Ingredient (Trade Name) | Ex. 5c | | Ex. 5d | |
|---|---|---|---|---|
| | Amt [g] | Solids [%] | Amt [g] | Solids [%] |
| Rivastigmine base | 3.51 | 17.53 | 3.54 | 17.67 |
| Silicone acrylic hybrid pressure sensitive adhesive in n-heptane Solids content of 46.7% by weight (PSA SilAc 7-6101 from Dow Corning Healthcare) | 35.37 | 82.47 | — | — |
| Silicone acrylic hybrid pressure sensitive adhesive in ethyl acetate Solids content of 50.5% by weight (PSA SilAc 7-6102 from Dow Corning Healthcare) | — | — | 32.67 | 82.33 |
| Total | 38.88 | 100.0 | 36.21 | 100.0 |
| Area Weight [g/m$^2$] | 102.0 | | 100.5 | |
| Loading API [µg/cm$^2$] | 1788 | | 1776 | |

Preparation of the Coating Composition

A beaker was loaded with the silicone acrylic hybrid pressure-sensitive adhesive having a solids content of about 50% by weight (PSA SilAc 7-6302 from Dow Corning Healthcare for Ex. 5a and 5b, PSA SilAc 7-6101 from Dow Corning Healthcare Ex. 5c, or PSA SilAc 7-6102 from Dow Corning Healthcare 5d). The rivastigmine base and, if applicable (Ex. 5a), the additional adhesive was added under stirring. The mixture was stirred at about 800 rpm (about 900 rpm for Ex. 5b to 5d) until a homogenous mixture was obtained (at least 20 min).

Coating of the Coating Composition

The resulting rivastigmine-containing coating composition was coated within less than 24 h after the rivastigmine-containing mixture was finished on an adhesively equipped foil (Scotchpak 9755 AB1F) using hand over knife lab coating equipment, using an erichson coater. The solvent was removed by drying in a first step at about room temperature (23±2° C.) for about 10 min, followed by a second drying step at about 60° C. for about 20 min.

The coating thickness was chosen such that removal of the solution results in an area weight of the rivastigmine-containing layer of about 93.1 (Ex. 5a), 107.7 (Ex. 5b), 102.0 (Ex. 5c), and 100.5 (Ex. 5d) g/m$^2$. The dried film was then laminated with a backing layer (FO PET 23 µm transparent).

Preparation of the TTS (Concerning all Examples)

See Example 1.

Measurement of Permeated Amount

The permeated amount of TTS prepared according to Examples 5a-d and of the commercially available Exelon® TTS was determined by experiments in accordance with the EMA Guideline on quality of transdermal patches (adopted Oct. 23, 2014) carried out with a 10.0 ml Franz diffusion cell, wherein EVA-membrane (9% vinyl acetate; Scotchpak Cotran 9702 from 3M) having a thickness of 50 µm was used. Diecuts with an area of release of 1.156 cm$^2$ were punched from the TTS. The rivastigmine permeated amount in the receptor medium of the Franz diffusion cell (phosphate buffer solution pH 5.5 with 0.1% sodium azide as antibacteriological agent) at a temperature of 32±1° C. was measured and the corresponding cumulated amount at 24 hours was calculated.

Figure 5:
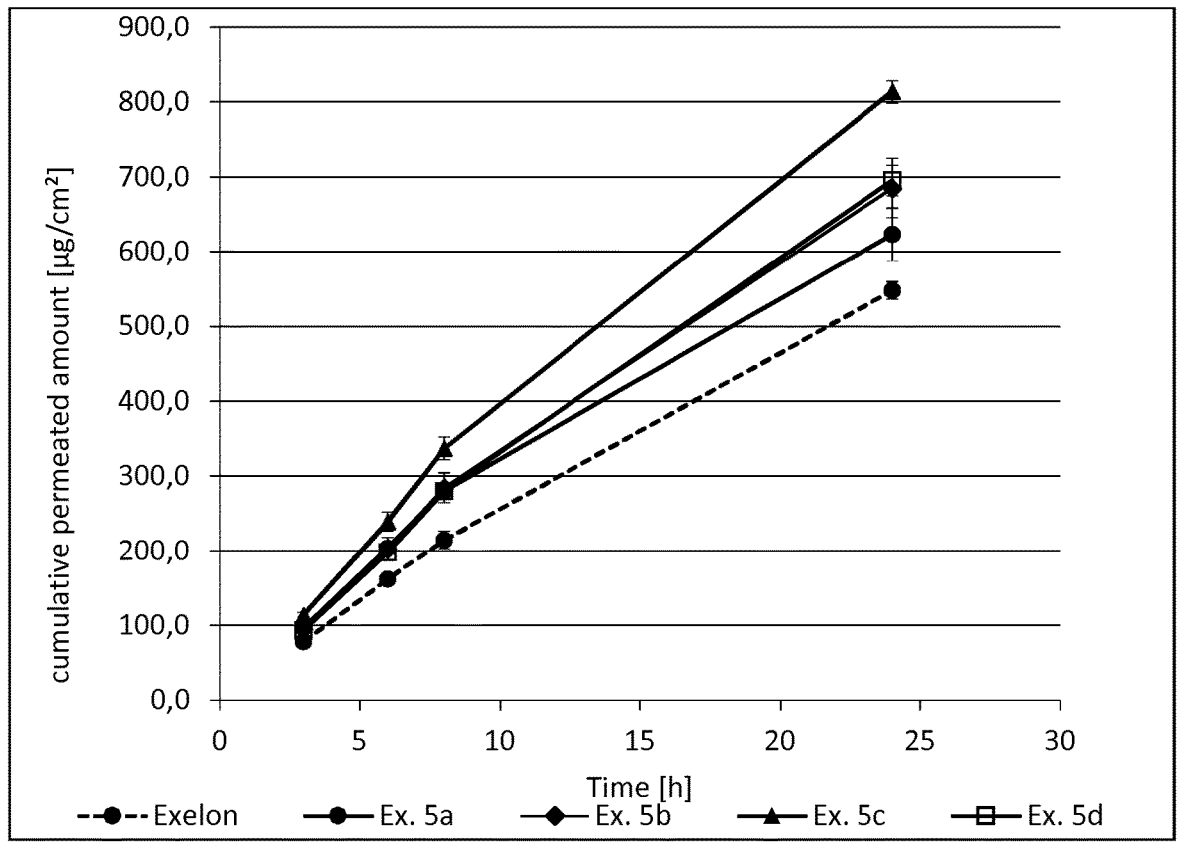
FIG. 5 depicts the rivastigmine cumulative permeated amount of TTS prepared according to Examples 5a-d and Exelon.

The results are shown in Tables 5.2 and FIG. 5.

TABLE 5.2

| | Permeated amount with SD [µg/cm$^2$] | | | | | | | | |
|---|---|---|---|---|---|---|---|---|---|
| Elapsed | Ex. 5a (n = 3) | | Ex. 5b (n = 3) | | Ex. 5c (n = 3) | | Ex. 5d (n = 3) | | Exelon ® (n = 3) | |
| time [h] | Amt | SD | Amt | SD | Amt | SD | Amot | SD | Amt | SD |
| 3 | 97.14 | 1.56 | 94.9 | 8.8 | 114.09 | 3.45 | 93.71 | 3.69 | 78.02 | 0.68 |
| 6 | 105.68 | 1.73 | 107.26 | 7.12 | 124.93 | 9.12 | 104.83 | 6.52 | 83.76 | 0.77 |
| 8 | 77.13 | 0.76 | 82.5 | 4.58 | 97.92 | 3.81 | 81.65 | 3.69 | 52.75 | 11.25 |
| 24 | 343.11 | 36.25 | 400.3 | 26.75 | 476.69 | 9.66 | 415.22 | 11.53 | 333.42 | 3.95 |
| Cum. at 24 h | 623.06 | 35.4 | 684.96 | 39.9 | 813.63 | 15.4 | 695.41 | 20.3 | 547.95 | 11.7 |

Example 6a-d

Coating Composition

The formulation of the rivastigmine-containing coating composition of Examples 6a-d are summarized in Table 6.1a and 6.1b below. The %-values refer to the amounts in % by weight.

TABLE 6.1

| Ingredient (Trade Name) | Ex. 6a | | Ex. 6b | |
|---|---|---|---|---|
| | Amt [g] | Solids [%] | Amt [g] | Solids [%] |
| Rivastigmine base | 10.03 | 20.04 | 6.00 | 19.94 |
| Silicone acrylic hybrid pressure sensitive adhesive in n-heptane; Solids content of 46.7% by weight (PSA SilAc 7-6101 from Dow Corning Healthcare) | 85.67 | 79.96 | 38.54 | 59.83 |
| Silicone adhesive in n-heptane Solids content of 72.8% by weight (DOW CORNING ® BIO-PSA Q7-4201) | — | — | 8.36 | 20.23 |
| Total | 95.7 | 100.0 | 52.9 | 100.0 |
| Area Weight [g/m$^2$] | | 90.9 | | 90.0 |
| Loading API [µg/cm$^2$] | | 1822 | | 1795 |

| Ingredient (Trade Name) | Ex. 6c | | Ex. 6d | |
|---|---|---|---|---|
| | Amt [g] | Solids [%] | Amt [g] | Solids [%] |
| Rivastigmine base | 10.00 | 20.00 | 10.00 | 19.80 |
| Silicone acrylic hybrid pressure sensitive adhesive in ethyl acetate Solids content of 50.3% by weight (PSA SilAc 7-6302 from Dow Corning Healthcare) | 59.64 | 60.00 | 59.68 | 59.45 |
| Acrylate adhesive in ethyl acetate Solids content of 35.9% by weight (DURO-TAK ® 387-2353) | 27.85 | 20.00 | — | — |
| Acrylate adhesive in ethyl acetate Solids content of 39.1% by weight (DURO-TAK ® 387-4098) | — | — | 26.80 | 20.75 |
| Total | 97.49 | 100.0 | 96.48 | 100.0 |
| Area Weight [g/m$^2$] | | 98.7 | | 91.4 |
| Loading API [µg/cm$^2$] | | 1973 | | 1810 |

Preparation of the Coating Composition

A beaker was loaded with the silicone acrylic hybrid pressure-sensitive adhesive having a solids content of about 50% by weight (PSA SilAc 7-6101 from Dow Corning Healthcare for Ex. 6a and 6b or PSA SilAc 7-6302 from Dow Corning Healthcare for Ex. 6c and 6d) and, if applicable (Ex. 6b, 6c, and 6d) the additional adhesive and homogenized for about 20 min. The rivastigmine base was added under stirring and under nitrogen flush (Ex. 6a and 6b). The mixture was stirred at about 500 rpm (Ex. 4a to 6c) or about 800 rpm (Ex. 6d) until a homogenous mixture was obtained (at least 20 min).

Coating of the Coating Composition

The resulting rivastigmine-containing coating composition was coated within less than 24 h after the rivastigmine-containing mixture was finished on an adhesively equipped foil (Scotchpak 9755 AB1F) using hand over knife lab coating equipment, using an erichson coater. The solvent was removed by drying in a first step at about room temperature (23±2° C.) for about 10 min, followed by a second drying step at about 60° C. (Ex 6a, 6c, and 6d) or 70° C. (Ex. 6b) for about 10 min (Ex. 6a to 6c) or for about 20 min (Ex. 6d).

The coating thickness was chosen such that removal of the solution results in an area weight of the rivastigmine-containing layer of about 90.9 (Ex. 6a), 90.0 (Ex. 6b), 98.7 (Ex. 6c), and 91.4 (Ex. 6d) g/m$^2$. The dried film was then laminated with a backing layer (FO PET 23 µm beige).

Preparation of the TTS (Concerning all Examples)

See Example 1.

Measurement of Permeated Amount

The permeated amount of TTS prepared according to Examples 6a-d and of the commercially available Exelon® TTS was determined by experiments in accordance with the EMA Guideline on quality of transdermal patches (adopted Oct. 23, 2014) carried out with a 10.0 ml Franz diffusion cell, wherein EVA-membrane (9% vinyl acetate; Nitroderm TTS K-Membrane 343 mm from PetroplastVinora AG) having a thickness of 50 µm was used. Diecuts with an area of release of 1.118 cm$^2$ were punched from the TTS. The rivastigmine permeated amount in the receptor medium of the Franz diffusion cell (phosphate buffer solution pH 5.5 with 0.1% sodium azide as antibacteriological agent) at a temperature of 32±1° C. was measured and the corresponding cumulated amount at 24 hours was calculated.

Figure 6:
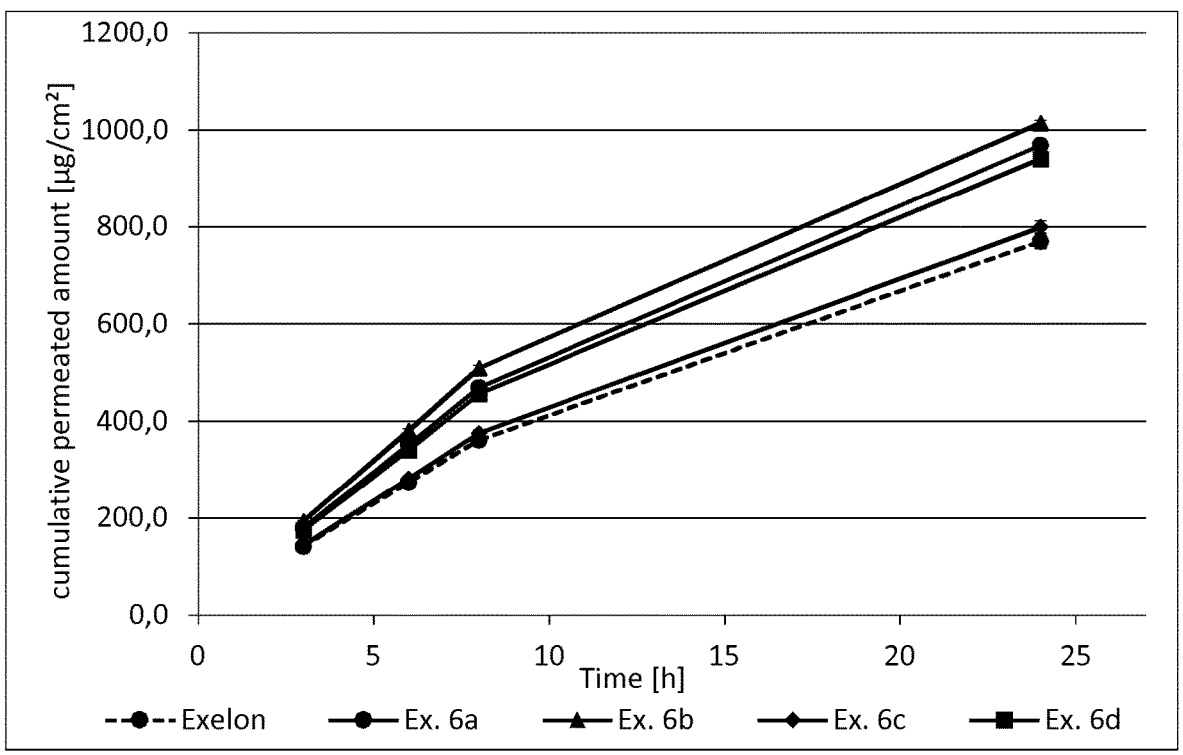
FIG. 6 depicts the rivastigmine cumulative permeated amount of TTS prepared according to Examples 6a-d and Exelon.

The results are shown in Tables 6.2 and FIG. 6.

TABLE 6.2

| | Permeated amount with SD [μg/cm$^2$] | | | | | | | | |
|---|---|---|---|---|---|---|---|---|---|
| | Ex. 6a (n = 3) | | Ex. 6b (n = 3) | | Ex. 6c (n = 3) | | Ex. 6d (n = 3) | | Exelon ® (n = 3) |
| Elapsed time [h] | Amt | SD | Amt | SD | Amt | SD | Amot | SD | Amt SD |
| 3 | 178.59 | 4.84 | 192.61 | 2.36 | 143.63 | 4.09 | 174.06 | 5.4 | 141.32 7.77 |
| 6 | 173.35 | 1.43 | 187.99 | 2.01 | 138.2 | 1.45 | 166.44 | 4.81 | 132.31 3.54 |
| 8 | 117.09 | 2.37 | 128.68 | 1.69 | 93.37 | 1.71 | 115.32 | 2.87 | 86.78 1.38 |
| 24 | 499.49 | 0.86 | 505.02 | 4.55 | 424.02 | 6.86 | 484.43 | 3.74 | 409.43 5.86 |
| Cum. at 24 h | 968.52 | 9.14 | 1014.3 | 5.26 | 799.22 | 12.9 | 940.25 | 15.6 | 769.84 16.0 |

Example 7a-d

Coating Composition

The formulation of the rivastigmine-containing coating composition of Examples 7a-d are summarized in Table 7.1a and 7.1b below. The %-values refer to the amounts in % by weight.

TABLE 7.1a

| | Ex. 7a | | Ex. 7b | |
|---|---|---|---|---|
| Ingredient (Trade Name) | Amt [g] | Solids [%] | Amt [g] | Solids [%] |
| Rivastigmine base | 10.00 | 19.99 | 10.02 | 20.04 |
| Silicone acrylic hybrid pressure sensitive adhesive in ethyl acetate Solids content of 50.5% by weight (PSA SilAc 7-6102 from Dow Corning Healthcare) | 79.25 | 80.01 | 59.4 | 60.01 |
| Silicone adhesive in n-heptane Solids content of 61.9% by weight (DOW CORNING ® BIO-PSA Q7-4202) | — | — | 16.11 | 19.95 |
| Total | 89.25 | 100.0 | 85.53 | 100.0 |
| Area Weight [g/m$^2$] | | 97.8 | | 93.9 |
| Loading API [μg/cm$^2$] | | 1955 | | 1882 |

TABLE 7.1b

| | Ex. 7c | | Ex. 7d | |
|---|---|---|---|---|
| Ingredient (Trade Name) | Amt [g] | Solids [%] | Amt [g] | Solids [%] |
| Rivastigmine base | 10.00 | 20.00 | 8.78 | 17.54 |
| Silicone acrylic hybrid pressure sensitive adhesive in n-heptane Solids content of 50.2% by weight (PSA Sil Ac 7-6301 from Dow Corning Healthcare) | 79.68 | 80.00 | — | — |
| Silicone acrylic hybrid pressure sensitive adhesive in ethyl acetate Solids content of 46.7% by weight (PSA SilAc 7-6101 from Dow Corning Healthcare) | — | — | 88.38 | 82.46 |
| Total | 89.68 | 100.0 | 97.16 | 100.0 |
| Area Weight [g/m$^2$] | | 88.1 | | 105.8 |
| Loading API [μg/cm$^2$] | | 1762 | | 1856 |

Preparation of the Coating Composition

A beaker was loaded with the silicone acrylic hybrid pressure-sensitive adhesive having a solids content of about 50% by weight (PSA SilAc 7-6102 from Dow Corning Healthcare for Ex. 7a and 7b, PSA SilAc 7-6301 from Dow Corning Healthcare Ex. 7c, or PSA SilAc 7-6101 from Dow Corning Healthcare 7d) and, if applicable (Ex. 7b) the additional adhesive was added and the mixture was homogenized. The rivastigmine base was added under stirring and, if applicable under nitrogen flush (Ex. 7c and 7d). The mixture was stirred at about 500 rpm (about 800 rpm for Ex. 7c) until a homogenous mixture was obtained (at least 20 min).

Coating of the Coating Composition

The resulting rivastigmine-containing coating composition was coated within less than 24 h after the rivastigmine-containing mixture was finished on an adhesively equipped foil (Scotchpak 9755 AB1F for Ex. 7a to 7c; Scotchpak 1022 TEPA for Ex. 7d) using hand over knife lab coating equipment, using an erichson coater. The solvent was removed by drying in a first step at about room temperature (23±2° C.) for about 10 min, followed by a second drying step at about 60° C. for about 10 min.

The coating thickness was chosen such that removal of the solution results in an area weight of the rivastigmine-containing layer of about 97.8 (Ex. 7a), 93.9 (Ex. 7b), 88.1 (Ex. 7c), and 105.8 (Ex. 7d) g/m$^2$. The dried film was then laminated with a backing layer (FO PET 23 μm beige).

Preparation of the TTS (Concerning all Examples)

See Example 1.

Measurement of Permeated Amount

The permeated amount of TTS prepared according to Examples 7a-d and of the commercially available Exelon® TTS was determined by experiments in accordance with the EMA Guideline on quality of transdermal patches (adopted Oct. 23, 2014) carried out with a 10.0 ml Franz diffusion cell, wherein EVA-membrane (9% vinyl acetate; Nitroderm TTS K-Membrane 343 mm from PetroplastVinora AG) having a thickness of 50 μm was used. Diecuts with an area of release of 1.118 cm$^2$ were punched from the TTS. The rivastigmine permeated amount in the receptor medium of the Franz diffusion cell (phosphate buffer solution pH 5.5 with 0.1% sodium azide as antibacteriological agent) at a temperature of 32±1° C. was measured and the corresponding cumulated amount at 24 hours was calculated.

Figure 7:
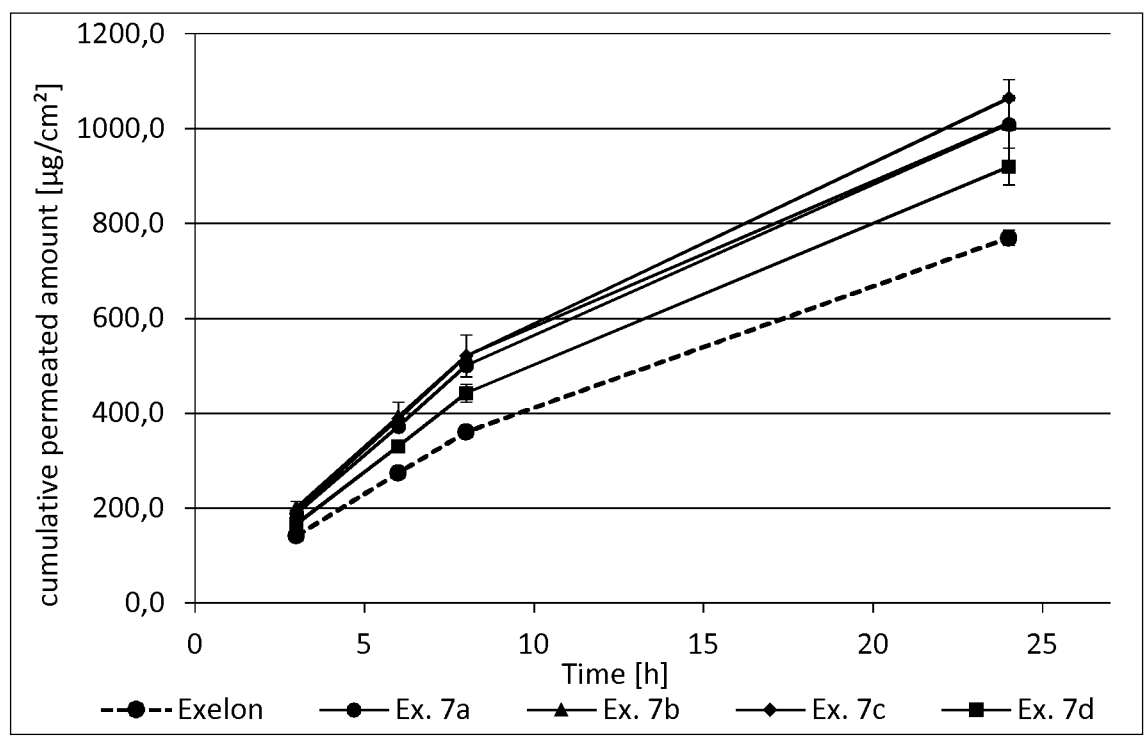
FIG. 7 depicts the rivastigmine cumulative permeated amount of TTS prepared according to Examples 7a-d and Exelon.

The results are shown in Tables 7.2 and FIG. 7.

TABLE 7.2

| Elapsed time [h] | Ex. 7a (n = 3) | | Ex. 7b (n = 3) | | Ex. 7c (n = 3) | | Ex. 7d (n = 3) | |
|---|---|---|---|---|---|---|---|---|
| | Amt | SD | Amt | SD | Amt | SD | Amt | SD |
| 3 | 188.84 | 6.61 | 201.61 | 11.83 | 194.9 | 3.51 | 166.9 | 6.62 |
| 6 | 183.82 | 2.58 | 191.09 | 20.38 | 194.16 | 2.68 | 163.53 | 7.13 |
| 8 | 128.37 | 2.96 | 128.06 | 14.22 | 132.06 | 1.06 | 111.98 | 5.39 |
| 24 | 508.67 | 4.2 | 490.65 | 51.07 | 543.48 | 3.51 | 477.85 | 20.93 |
| Cum. at 24 h | 1009.4 | 3.73 | 1011.41 | 91.7 | 1064.6 | 5.06 | 920.26 | 38.9 | permeated amount with SD [µg/cm$^2$]

The Invention Relates in Particular to the Following Further Items

1. Transdermal therapeutic system for the transdermal administration of rivastigmine comprising a rivastigmine-containing layer structure, said rivastigmine-containing layer structure comprising:
  A) a backing layer; and
  B) a rivastigmine-containing layer;
wherein the transdermal therapeutic system comprises a silicone acrylic hybrid polymer.
2. Transdermal therapeutic system according to item 1, wherein the rivastigmine-containing layer is a rivastigmine-containing matrix layer comprising:
  1. rivastigmine; and
  2. the silicone acrylic hybrid polymer.
3. Transdermal therapeutic system according to any one of items 1 or 2,
wherein the rivastigmine-containing layer structure is a rivastigmine-containing self-adhesive layer structure and preferably does not comprise an additional skin contact layer.
4. Transdermal therapeutic system according to any one of items 1 to 3,
wherein the silicone acrylic hybrid polymer is a silicone acrylic hybrid pressure-sensitive adhesive.
5. Transdermal therapeutic system according to any one of items 1 to 4,
wherein the rivastigmine-containing layer structure contains a therapeutically effective amount of rivastigmine.
6. Transdermal therapeutic system according to any one of items 1 to 5,
wherein the rivastigmine in the rivastigmine-containing layer structure is present in the form of the free base.
7. Transdermal therapeutic system according to any one of items 1 to 6,
wherein the amount of rivastigmine contained in the rivastigmine-containing layer structure ranges from 0.5 to 5 mg/cm$^2$, preferably from 1 to 3 mg/cm$^2$.
8. Transdermal therapeutic system according to any one of items 1 to 7,
wherein the rivastigmine-containing layer comprises rivastigmine in an amount of from 5 to 30%, more preferably from 7 to 28%, most preferably from 10 to 25% by weight based on the total weight of the rivastigmine-containing layer.
9. Transdermal therapeutic system according to any one of items 1 to 8,
wherein the amount of the silicone acrylic hybrid polymer ranges from 35 to 95%, preferably from 40 to 93%, most preferably from 45 to 90% by weight based on the total weight of the rivastigmine-containing layer.
10. Transdermal therapeutic system according to any one of items 1 to 9,
wherein the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.
11. Transdermal therapeutic system according to any one of items 1 to 9,
wherein the silicone acrylic hybrid polymer is a silicone acrylic hybrid pressure-sensitive adhesive obtainable from
  (a) a silicon-containing pressure-sensitive adhesive composition comprising acrylate or methacrylate functionality.
12. Transdermal therapeutic system according to any one of items 1 to 9 or 11,
wherein the silicone acrylic hybrid polymer is a silicone acrylic hybrid pressure-sensitive adhesive comprising the reaction product of
  (a) a silicon-containing pressure-sensitive adhesive composition comprising acrylate or methacrylate functionality;
  (b) an ethylenically unsaturated monomer; and
  (c) an initiator.
13. Transdermal therapeutic system according to any one of items 11 or 12,
wherein the silicon-containing pressure-sensitive adhesive composition comprising acrylate or methacrylate functionality comprises the condensation reaction product of
  (a1) a silicone resin, and
  (a2) a silicone polymer, and
  (a3) a silicon-containing capping agent comprising acrylate or methacrylate functionality.
14. Transdermal therapeutic system according to any one of items 11 to 13,
wherein the silicon-containing pressure-sensitive adhesive composition comprising acrylate or methacrylate functionality comprises the condensation reaction product of
  (a1) a silicone resin, and
  (a2) a silicone polymer, and
  (a3) a silicon-containing capping agent comprising acrylate or methacrylate functionality,
wherein said silicon-containing capping agent is of the general formula $XYR'_bSiZ_{3-b}$, wherein X is a monovalent radical of the general formula AE, where E is —O— or —NH— and A is an acryl group or methacryl group, Y is a divalent alkylene radical having from 1 to 6 carbon atoms, R' is a methyl or a phenyl radical, Z is a monovalent hydrolysable organic radical or halogen, and b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein the silicon-containing capping agent reacts with the pressure-sensitive adhesive after the silicone resin and silicone polymer have been condensation reacted to form the pressure-sensitive adhesive, or the silicon-containing capping agent reacts in situ with the silicone resin and silicone polymer.

15. Transdermal therapeutic system according to any one of items 12 to 14,
wherein the ethylenically unsaturated monomer is selected from the group consisting of aliphatic acrylates, aliphatic methacrylates, cycloaliphatic acrylates, cycloaliphatic methacrylates, and combinations thereof, each of said compounds having up to 20 carbon atoms in the alkyl radical.

16. Transdermal therapeutic system according to any one of items 12 to 15,
wherein the reaction product of
(a) the silicon-containing pressure-sensitive adhesive composition comprising acrylate or methacrylate functionality;
(b) the ethylenically unsaturated monomer; and
(c) the initiator
contains a continuous, silicone external phase and a discontinuous, acrylic internal phase.

17. Transdermal therapeutic system according to any one of items 12 to 15,
wherein the reaction product of
(a) the silicon-containing pressure-sensitive adhesive composition comprising acrylate or methacrylate functionality;
(b) the ethylenically unsaturated monomer; and
(c) the initiator
contains a continuous, acrylic external phase and a discontinuous, silicone internal phase.

18. Transdermal therapeutic system according to any one of items 1 to 16,
wherein the silicone acrylic hybrid polymer in the rivastigmine-containing layer contains a continuous, silicone external phase and a discontinuous, acrylic internal phase, or a continuous, acrylic external phase and a discontinuous, silicone internal phase,
and wherein preferably the rivastigmine is present in the rivastigmine-containing layer in an amount of from 15 to 25% by weight based on the total weight of the rivastigmine-containing layer.

19. Transdermal therapeutic system according to any one of items 1 to 18,
wherein the rivastigmine-containing layer further comprises a non-hybrid polymer.

20. Transdermal therapeutic system according to item 19,
wherein the non-hybrid polymer is a pressure-sensitive adhesive based on polysiloxanes, acrylates, or polyisobutylenes, preferably based on polysiloxanes or acrylates.

21. Transdermal therapeutic system according to any one of items 19 or 20,
wherein the non-hybrid polymer is contained in the rivastigmine-containing layer in an amount of from 5 to 40%, preferably from 8 to 35% by weight based on the total weight of the rivastigmine-containing layer.

22. Transdermal therapeutic system according to any one of items 19 to 21,
wherein the weight ratio of the silicone acrylic hybrid polymer to the non-hybrid polymer is from 8:1 to 1:2, preferably from 7:1 to 1:1.

23. Transdermal therapeutic system according to any one of items 1 to 22,
wherein the rivastigmine-containing layer does not comprise a permeation enhancer or solubilizer.

24. Transdermal therapeutic system according to any one of items 1 to 23,
wherein the area weight of the rivastigmine-containing layer ranges from 40 to 250 g/m$^2$, preferably from 50 to 200 g/m$^2$.

25. Transdermal therapeutic system according to any one of items 1 to 24,
wherein the area of release ranges from 1 to 30 cm$^2$, preferably from 2 to 22 cm$^2$.

26. Transdermal therapeutic system according to any one of items 1 to 25,
wherein the transdermal therapeutic system provides by transdermal delivery a mean release rate of from 150 to 3500 μg/cm$^2$*day, preferably from 200 to 3000 μg/cm$^2$*day rivastigmine over about 24 hours of administration.

27. Transdermal therapeutic system according to any one of items 1 to 26,
wherein the transdermal therapeutic system provides by transdermal delivery at steady state a plasma concentration of rivastigmine of from 1 to 25 ng/ml, preferably from 1 to 20 ng/ml.

28. Transdermal therapeutic system according to any one of items 1 to 27,
having an AUC$_{24h}$ of about 10 to 450 ng*h/ml, preferably of about 20 to 340 ng*h/ml, after repeated once daily administration.

29. Transdermal therapeutic system according to any one of items 1 to 28,
having a C$_{max}$ of about 0.5 to 30 ng/ml, preferably of about 1 to 25 ng/ml, after applying the transdermal therapeutic system on the skin of the patient.

30. Transdermal therapeutic system according to any one of items 1 to 29,
having a t$_{max}$ of about 3 to 15 hours, preferably of about 5 to 10 hours, after applying the transdermal therapeutic system on the skin of the patient.

31. Transdermal therapeutic system according to any one of items 1 to 30,
providing a cumulative permeated amount of rivastigmine as measured in a Franz diffusion cell with an EVA membrane of about 300 to 1200 μg/cm$^2$ over a time period of about 24 hours.

32. Transdermal therapeutic system according to any one of items 1 to 31 for use in a method of treating a human patient, preferably for use in a method of preventing, treating, or delaying of progression of Alzheimer's disease, dementia associated with Parkinson's disease, and/or symptoms of traumatic brain injury.

33. Transdermal therapeutic system according to any one of items 1 to 31 for use in a method of treating a human patient, preferably for use in a method of treating mild to moderate dementia caused by Alzheimer's or Parkinson's disease.

34. Transdermal therapeutic system for use according to any one of items 32 or 33, wherein the transdermal therapeutic system is applied to the skin of the patient for a dosing interval of at least 24 hours, preferably about 24 hours.

35. Method of treating a human patient, in particular preventing, treating, or delaying of progression of Alzheimer's disease, dementia associated with Parkinson's disease, and/or symptoms of traumatic brain injury, by applying a transdermal therapeutic system as defined in any one of items 1 to 31 to the skin of the patient.

36. Method of treating a human patient, in particular treating a mild to moderate dementia caused by Alzheimer's and Parkinson's disease, by applying a transdermal therapeutic system as defined in any one of items 1 to 31 to the skin of the patient.

37. Method of treating a human patient according to any one of items 35 or 36, wherein the transdermal therapeutic system is applied to the skin of the patient for a dosing interval of at least 24 hours, preferably about 24 hours.

38. A process for manufacturing a rivastigmine-containing layer for use in a transdermal therapeutic system according to any one of items 1 to 31 comprising the steps of:
1) combining at least the components
  1. rivastigmine in an amount such that the amount of rivastigmine in the resulting rivastigmine-containing layer is from 10 to 25% by weight based on the total weight of the rivastigmine-containing layer;
  2. a silicone acrylic hybrid polymer; and
  3. optionally at least one additional non-hybrid polymer and/or additive;
to obtain a coating composition;
2) coating the coating composition onto the backing layer or release liner; and
3) drying the coated coating composition to form the rivastigmine-containing layer.

39. Process for manufacturing a rivastigmine-containing layer according to item 38, wherein the silicone acrylic hybrid polymer is provided as a solution, wherein the solvent is ethyl acetate or n-heptane.

40. Transdermal therapeutic system obtainable by a process in accordance with any one of items 38 or 39.

41. Transdermal therapeutic system for the transdermal administration of rivastigmine comprising a rivastigmine-containing layer structure, said rivastigmine-containing layer structure comprising:
A) a backing layer; and
B) a rivastigmine-containing layer comprising:
  1. rivastigmine in an amount of from 10 to 25% by weight based on the total weight of the rivastigmine-containing layer;
  2. a silicone acrylic hybrid polymer containing a continuous, silicone external phase and a discontinuous, acrylic internal phase, in an amount of from 45 to 90% by weight based on the total weight of the rivastigmine-containing layer; and
  3. optionally a pressure-sensitive adhesive based on polysiloxanes in an amount of from 10 to 30% by weight based on the total weight of the rivastigmine-containing layer;
wherein said rivastigmine-containing layer is the skin contact layer;
and wherein the area weight of said rivastigmine-containing layer ranges from 60 to 180 g/m².

42. Transdermal therapeutic system for the transdermal administration of rivastigmine comprising a rivastigmine-containing layer structure, said rivastigmine-containing layer structure comprising:
A) a backing layer; and
B) a rivastigmine-containing layer comprising:
  1. rivastigmine in an amount of from 10 to 25% by weight based on the total weight of the rivastigmine-containing layer;
  2. a silicone acrylic hybrid polymer containing a continuous, acrylic external phase and a discontinuous, silicone internal phase, in an amount of from 40 to 90% by weight based on the total weight of the rivastigmine-containing layer; and
  3. optionally a pressure-sensitive adhesive based on acrylates in an amount of from 5 to 40% by weight based on the total weight of the rivastigmine-containing layer;
wherein said rivastigmine-containing layer is the skin contact layer;
and wherein the area weight of said rivastigmine-containing layer ranges from 60 to 180 g/m².

The invention claimed is:

1. A transdermal therapeutic system for the transdermal administration of rivastigmine comprising a rivastigmine-containing layer structure, said rivastigmine-containing layer structure comprising:
A) a backing layer; and
B) a rivastigmine-containing layer;
wherein the transdermal therapeutic system comprises a silicone acrylic hybrid polymer comprising repeating units of a silicone sub-species and an acrylate-sub species,
wherein the silicone acrylic hybrid polymer is a silicone acrylic hybrid pressure-sensitive adhesive comprising the reaction product of:
  (a) a silicon-containing pressure-sensitive adhesive composition comprising acrylate or methacrylate functionality;
  (b) an ethylenically unsaturated monomer; and
  (c) an initiator, and
wherein the transdermal therapeutic system provides a permeated amount of rivastigmine as measured in a Franz diffusion cell with EVA-membrane of:
  0 μg/cm² to 240 μg/cm² in hours 0 to 3;
  80 μg/cm² to 350 μg/cm² from hour 3 to hour 8; and
  210 μg/cm² to 560 μg/cm² from hour 8 to hour 24.

2. The transdermal therapeutic system according to claim 1, wherein the rivastigmine-containing layer is a rivastigmine-containing matrix layer comprising:
  (i) rivastigmine; and
  (ii) the silicone acrylic hybrid polymer.

3. The transdermal therapeutic system according to claim 1, wherein the rivastigmine-containing layer structure is a rivastigmine-containing self-adhesive layer structure.

4. The transdermal therapeutic system according to claim 1, wherein the silicone acrylic hybrid polymer is a silicone acrylic hybrid pressure-sensitive adhesive.

5. The transdermal therapeutic system according to claim 1, wherein the rivastigmine-containing layer structure contains from 0.5 to 5 mg/cm² rivastigmine.

6. The transdermal therapeutic system according to claim 1, wherein the rivastigmine-containing layer comprises at least one or more of: (a) from 5 to 30% rivastigmine by weight of the rivastigmine-containing layer; and (b) from 35 to 95% silicone acrylic hybrid polymer by weight of the rivastigmine-containing layer.

7. The transdermal therapeutic system according to claim 1, wherein the silicone acrylic hybrid polymer comprises a reaction product of a silicone polymer, a silicone resin and an acrylic polymer, wherein the acrylic polymer is covalently self-crosslinked and covalently bound to the silicone polymer, the silicone resin, or both the silicone polymer and the silicone resin.

8. The transdermal therapeutic system according to claim 1, wherein the reaction product of
  (a) the silicon-containing pressure-sensitive adhesive composition comprising acrylate or methacrylate functionality;
  (b) the ethylenically unsaturated monomer; and
  (c) the initiator;
contains a continuous, silicone external phase and a discontinuous, acrylic internal phase; or
contains a continuous, acrylic external phase and a discontinuous, silicone internal phase.

9. The transdermal therapeutic system according to claim 1, wherein the silicone acrylic hybrid polymer in the rivastigmine-containing layer contains a continuous, silicone external phase and a discontinuous, acrylic internal phase; or a continuous, acrylic external phase and a discontinuous, silicone internal phase, and wherein the rivastigmine-containing layer comprises from 15 to 25% rivastigmine by weight of the rivastigmine-containing layer.

10. The transdermal therapeutic system according to claim 1, wherein the rivastigmine-containing layer further comprises a non-hybrid polymer selected from the group consisting of polysiloxanes, acrylates, and polyisobutylenes.

11. The transdermal therapeutic system according to claim 10, wherein the non-hybrid polymer comprises from 5 to 40% by weight of the rivastigmine-containing layer, and wherein the weight ratio of the silicone acrylic hybrid polymer to the non-hybrid polymer is from 8:1 to 1:2.

12. The transdermal therapeutic system according to claim 1, wherein the rivastigmine-containing layer has an area weight ranging from 40 to 250 g/m$^2$, and an area of release ranging from 1 to 30 cm$^2$.

13. The transdermal therapeutic system according to claim 1, wherein the transdermal therapeutic system provides by transdermal delivery a mean release rate of from 150 to 3500 μg/cm$^2$ rivastigmine over about 24 hours of administration.

14. The transdermal therapeutic system according to claim 1, wherein the transdermal therapeutic system provides by transdermal delivery at steady state at least one pharmacokinetic parameter selected from the group consisting of:
   a plasma concentration of rivastigmine of from 1 to 25 ng/ml;
   an $AUC_{24h}$ of about 10 to 450 ng*h/ml after repeated once daily administration;
   a $C_{max}$ of about 0.5 to 30 ng/ml after applying the transdermal therapeutic system on the skin of the patient; and
   a $t_{max}$ of about 3 to 15 hours after applying the transdermal therapeutic system on the skin of the patient.

15. A process for manufacturing a rivastigmine-containing layer for use in the transdermal therapeutic system according to claim 1 comprising:
   combining at least the components
      a. rivastigmine in an amount from 10 to 25% by weight of the resulting rivastigmine-containing layer;
      b. a silicone acrylic hybrid polymer; and
      c. optionally at least one additional non-hybrid polymer and/or additive; to obtain a coating composition;
   coating the coating composition onto the backing layer or release liner; and
   drying the coated coating composition to form the rivastigmine-containing layer.

\* \* \* \* \*